(12) United States Patent
Gamache

(10) Patent No.: US 10,379,054 B2
(45) Date of Patent: Aug. 13, 2019

(54) MULTI-MODE PLASMA-BASED OPTICAL EMISSION GAS DETECTOR

(71) Applicant: Mecanique Analytique Inc., Thetford-Mines (CA)

(72) Inventor: Yves Gamache, Thetford-Mines (CA)

(73) Assignee: Mecanique Analytique Inc., Thetford-Mines (Quebec) (CA)

( * ) Notice: Subject to any disclaimer, the term of this patent is extended or adjusted under 35 U.S.C. 154(b) by 0 days.

(21) Appl. No.: 15/555,620

(22) PCT Filed: Mar. 2, 2016

(86) PCT No.: PCT/CA2016/050221
§ 371 (c)(1),
(2) Date: Sep. 5, 2017

(87) PCT Pub. No.: WO2016/141463
PCT Pub. Date: Sep. 15, 2016

(65) Prior Publication Data
US 2018/0038800 A1 Feb. 8, 2018

Related U.S. Application Data

(60) Provisional application No. 62/129,231, filed on Mar. 6, 2015.

(51) Int. Cl.
*G01J 3/30* (2006.01)
*G01N 21/67* (2006.01)
(Continued)

(52) U.S. Cl.
CPC ............. *G01N 21/67* (2013.01); *G01J 3/443* (2013.01); *G01N 21/01* (2013.01); *G01N 2201/023* (2013.01)

(58) Field of Classification Search
CPC ........ G01N 21/67; G01N 21/01; G01N 15/02; G01N 15/14; G01N 27/66; G01N 30/64; H01S 3/30; H01L 21/26; H01L 21/42
See application file for complete search history.

(56) References Cited

U.S. PATENT DOCUMENTS 5,570,179 A 10/1996 Weckstroem
2006/0290925 A1 12/2006 Nomine
(Continued)

FOREIGN PATENT DOCUMENTS

WO 2016/051357 A1 4/2016

OTHER PUBLICATIONS

International Search Report and Written Opinion for International Application No. PCT/CA2016/050221, dated Jun. 8, 2016.
(Continued)

*Primary Examiner* — Abdullahi Nur
(74) *Attorney, Agent, or Firm* — Eversheds Sutherland (US) LLP

(57) ABSTRACT

A plasma-based detector using optical spectroscopic techniques for analyzing the constituents of gas samples are provided. The detector includes a plasma-generating mechanism and a plasma-localizing mechanism. Electron-injecting electrodes may be provided in the plasma chamber of the detector. A Pressure control mechanism as well as a doping module may optionally be included. In accordance with some implementations, the collection, detection and analysis of light extracted from the plasma may enable one or more of various operation modes, such as an emission mode, an absorption mode, and indirect detection mode or a constant emission mode.

63 Claims, 11 Drawing Sheets

(51) Int. Cl.
   *G01N 21/01*   (2006.01)
   *G01J 3/443*   (2006.01)

(56) References Cited

U.S. PATENT DOCUMENTS

2009/0132206 A1    5/2009   Gamache et al.
2009/0196801 A1    8/2009   Mills
2018/0038832 A1*   2/2018   Gamache ............... G01N 27/66

OTHER PUBLICATIONS

European Patent Office, Supplementary Partial European Search Report, dated Sep. 3, 2018, 17 pages, Munich, Germany.

* cited by examiner

MULTI-MODE PLASMA-BASED OPTICAL EMISSION GAS DETECTOR

CROSS REFERENCE TO RELATED APPLICATIONS

This application claims the benefit of priority to U.S. Provisional Application No. 62/129,231, filed Mar. 6, 2015, which is incorporated by reference herein in its entirety, and is a 35 U.S.C. § 371 national stage application of PCT Patent Application No. PCT/CA2016/050221, filed Mar. 2, 2016, which is incorporated by reference in its entirety.

TECHNICAL FIELD

The technical field generally relates to gas detectors for chromatography applications and the like, and more particularly concerns plasma-based detectors having one or more plasma control features and operation modes.

BACKGROUND

Several types of gas detectors for detecting, measuring and/or analysing constituents of a gas sample are known in the art. For example, in the context of chromatographic systems, it is known to select a detector based on the application at hand, the type of carrier gas and impurities to be detected, the desired information, the required precision of the results, price considerations, etc. Gas detectors suitable for some chromatography applications include Flame Ionization Detectors (FID), Electron Capture Detectors (ECD), Thermal Conductivity Detectors (ECD), Photoionization Detectors (PID) and Mass spectrometers (MS), to name only a few.

There remains a need in the art for versatile gas detectors which can provide improvements over available devices and may be of use for different applications.

SUMMARY

Plasma-based detectors using optical spectroscopic techniques for analysing the constituents of gas samples are provided. In accordance with some embodiments, the plasma-based detector may be provided with one or more features allowing its use for different applications and in different operating conditions.

Such features may include mechanisms for plasma generation and stability improvement. In one aspect, a mechanism for generating a localizing field in the plasma chamber is preferably provided. In another aspect, electron-injecting electrodes may be provided in the plasma chamber. Pressure control mechanisms may also be provided and used to improve plasma control or enable plasma generation in hard to ionize gases.

Light detection and analysis features may be also be provided. In accordance with some implementations, the collection, detection and analysis of light extracted from the plasma may enable one or more of various operation modes, such as an emission mode, an absorption mode, or a power balance mode.

In accordance with one aspect, there is provided a plasma-based optical emission gas detector, comprising:
a plasma chamber traversed by a gas flow path allowing a flow of a gas sample through the plasma chamber;
a plasma-generating mechanism configured to apply a plasma-generating field across the plasma chamber intersecting the gas flow path so as to generate a plasma from said gas sample;
at least one window allowing optical emissions from said plasma to exit the plasma chamber therethrough; and a plasma-localizing mechanism configured to apply a plasma-localizing field across the plasma chamber and positioned such that the plasma-localizing field localizes the plasma within the plasma chamber in alignment with the at least one optical window.

In some embodiments, the plasma-localizing field is applied transversally to the plasma-generating field.

In some embodiments, the plasma-generating mechanism relies on a Dielectric Barrier Discharge. For example, the plasma-generating mechanism may include a pair of discharge electrodes extending parallelly on opposite sides of the plasma chamber and separated by a discharge gap, a pair of insulating dielectric barriers each extending within the discharge gap along a corresponding one of the discharge electrodes, and an alternating current generator providing an alternating discharge driving signal to the discharge electrodes. Each insulating layer of said pair may be defined by a wall of the plasma chamber. The plasma chamber may for example include a pair of opposite first walls associated with the plasma-generating mechanism and a pair of opposite second walls transversal to the first walls and associated with the plasma-localizing mechanism. In one embodiment, the plasma chamber has an hexagonal configuration defining top and bottom walls associated with the plasma-generating mechanism, a pair of opposite sides walls associated with the plasma-localizing mechanism and four remaining side walls each associated with one of the at least one window.

In some embodiments, the plasma-localizing mechanism may include a pair of localizing electrodes extending parallelly on opposite sides of the plasma chamber, the plasma-localizing field being an electrical field. The plasma-localizing mechanism may further comprises a power supply configured to apply a localizing drive signal on the localizing electrodes which may be a DC signal or which may comprise a DC component and an AC component synchronized with the discharge driving signal. Preferably, the localizing driving signal is controllable to align the plasma with a selected one of the at least one window in synchronicity with a passage of a predetermined impurity peak in the gas sample along the gas flow path.

In some embodiments, the plasma-localizing mechanism may include a pair of electromagnets extending parallelly on opposite sides of the plasma chamber, the plasma-localizing field being a magnetic field.

In some embodiments, the plasma-based optical emission gas detector may further include a pair of electron-injecting electrodes, each electrode of said pair having an extremity projecting within the plasma. Each electron-injecting electrode may for example have a needle or a flat-tip shape. The extremities of the electron-injecting electrodes of said pair preferably project within the plasma chamber from opposite sides thereof. In some variants, the plasma-based optical emission gas detector includes a gas inlet and a gas outlet defining opposite ends of said gas flow path, each of the electron-injection electrodes of said pair being inserted in the plasma chamber through a respective one of the gas inlet and gas outlet.

In some embodiments, the plasma-based optical emission gas detector may further comprise a pressure control mechanism configured to control a pressure within the plasma chamber over a continuous pressure range. For example, the continuous pressure range may substantially extend between vacuum pressure and atmospheric pressure.

In some embodiments, the plasma-based optical emission gas detector may further include:

at least one light-collecting assembly, each light collecting assembly collecting the optical emissions from said plasma exiting the plasma chamber through a corresponding one of the at least one window;
a light detection module configured to detect the optical emissions collected by the at least one light-collecting assembly; and
a processing module configured to process the optical emissions detected by the light detection module.

In some implementations each of the at least one light collecting assembly comprises an optical fiber collecting light from the corresponding one of the at least one window, and a lens provided on outside of the corresponding one of the at least one window and focussing the optical emissions transmitted therethrough into the corresponding optical fiber.

In some implementations, the light detection module includes at least one detection cartridge, each detection cartridge detecting the optical emissions collected by a corresponding one of the at least one light-collecting assembly. Each detection cartridge may include a photodiode converting the corresponding optical emissions into an electrical signal.

In some implementations, each of the at least one light collecting assembly or each of the at least one detection cartridge includes an optical filter transmitting through only a spectral range of interest.

In some embodiments, the at least one window consist in a plurality of windows, each of said windows being associated with optical emissions in a different spectral range. The plasma-localizing mechanism may be further configured to adapt the plasma-localizing field to align the plasma with a selected one of said windows in synchronization with a passage of a gas species emitting in the corresponding spectral range through the plasma chamber.

In some embodiments, the plasma-based optical emission detector may further include a plasma doping module configured to inject at least one dopant species to the gas sample flowing through the plasma chamber. The plasma-based optical emission detector may further comprise an injection tubing carrying the gas sample to the plasma chamber, and the plasma doping module may comprise an orifice in said injection tubing. Alternatively or additionally, the plasma doping module may include a permeation device. In another variant, the plasma doping module may include an electrically conducting tube inserted into the plasma chamber.

In some embodiments, the plasma-based optical emission detector includes, in combination:
a pressure control mechanism configured to control a pressure within the plasma chamber over a continuous pressure range;
a plasma doping module configured to inject at least one dopant species to the gas sample flowing through the plasma chamber
at least one light-collecting assembly, each light collecting assembly collecting the optical emissions from said plasma exiting the plasma chamber through a corresponding one of the at least one window;
a light detection module configured to detect the optical emissions collected by the at least one light-collecting assembly; and
a processing module configured to process the optical emissions detected by the light detection module, the processing module comprising a microcontroller in communication with the plasma-generating mechanism, the plasma-localizing mechanism, the pressure control mechanism and the plasma doping module.

The plasma-based optical emission detector may be operable in one, some or all of a plurality of modes comprising:
an emission mode wherein said optical emissions correspond to gas species to be measured in the gas sample;
an absorption mode wherein absorption of an interrogation light beam through the plasma is measured;
an indirect detection mode wherein the gas species to be measured in the gas sample is detected through optical emissions associated with at least one dopant provided in the plasma chamber by the plasma doping module; and
a constant emission mode wherein the light detection is used to continuously monitor the optical emissions from the plasma and a frequency of the plasma-generating mechanism is adjusted to maintain said optical emissions constant, the gas species to be measured in the gas sample being detected through a variation in said frequency.

In accordance with another aspect, there is provided a plasma-based gas detector, comprising a plasma chamber traversed by a gas flow path allowing a flow of a gas sample through said plasma chamber. The plasma-based gas detector further includes a plasma-generating mechanism configured to apply a plasma-generating field across the plasma chamber, the plasma-generating field intersecting the gas flow path so as to generate a plasma from said gas sample, the plasma occupying a plasma region within the plasma chamber. The plasma-based gas detector further includes a pair of electron-injecting electrodes, each electrode of said pair having an extremity projecting within the plasma region.

In some embodiments, each electron-injecting electrode has a needle or a flat-tip shape.

In some embodiments, the extremities of the electron-injecting electrodes of said pair project within the plasma chamber from opposite sides thereof.

In some embodiments, the plasma-based gas detector includes a gas inlet and a gas outlet defining opposite ends of said gas flow path, and each of the electron-injection electrodes of said pair are inserted in the plasma chamber through a respective one of the gas inlet and gas outlet.

In some embodiments, the plasma-based gas detector further comprises a pressure control mechanism configured to control a pressure within the plasma chamber. At least one of the electron-injecting electrodes may be an electrically conducting tube inserted into the plasma chamber and connectable to a dopant source to inject at least one dopant species to the gas sample flowing through the plasma chamber.

In accordance with another aspect, there is provided a method for generating a plasma in a plasma chamber of a plasma-based gas detector, the method comprising:
a) circulating a flow of a gas sample through the plasma chamber;
b) controlling a pressure inside the plasma chamber to a sub-atmospheric level;
c) applying a plasma-generating field across the plasma chamber intersecting the flow of gas sample so as to generate a plasma from the gas sample;
d) putting respective extremities of a pair of electron-injecting electrodes in contact with the plasma; and
e) applying a voltage on the electron-injecting electrode such that free electrons are injected within the plasma chamber.

In accordance with yet another aspect, there is also provided a method of detecting a gas species in a gas sample, comprising:

a) providing a plasma-based optical emission gas detector comprising a plasma chamber and a pressure control mechanism operable to control a pressure in the plasma chamber over a continuous pressure range;
b) selecting a pressure setting based on at least one sample characteristic associated with the gas sample;
c) circulating a flow of the gas sample through the plasma chamber;
d) generating a plasma from the gas sample in the plasma chamber;
e) controlling the pressure control mechanism to maintain the pressure in the plasma chamber at the selected pressure setting; and
f) measuring optical emissions from the plasma indicative of presence of the gas species.

In some embodiments, the continuous pressure range substantially extends between vacuum pressure and atmospheric pressure.

In some embodiments, the at least one sample characteristic comprises a volume of the gas sample flowing through the plasma chamber, an excitation potential of the gas species or a target residence time of the gas species in the plasma chamber.

In some embodiments, the pressure setting is selected in view of tuning an internal volume of the plasma chamber.

In some embodiments, the gas species has an ionization potential higher than an ionization potential of a carrier gas carrying said gas species though the plasma chamber.

In some embodiments, the controlling of step e) may involve using a feedback control loop. For example, the feedback control loop may comprise measuring a pressure of the gas sample downstream the plasma chamber and operating a pump in the pressure control mechanism if view of the measured pressure.

In some embodiments, the measuring of step f) may comprise measuring an intensity of said optical emissions at one or more wavelengths characteristic of the gas species.

In some embodiments, the generating a plasma of step of d) may comprises:
  i. putting respective extremities of a pair of electron-injecting electrodes in contact with the plasma; and
  ii. applying a voltage on the electron-injecting electrode such that free electrons are injected within the plasma chamber.

In accordance with yet another aspect, there is also provided a method of measuring a gas species in a gas sample, comprising:
a) providing a plasma-based optical emission gas detector comprising a plasma chamber and a plasma-generating mechanism comprising a pair of discharge electrodes and an alternating current generator providing an alternating discharge driving signal to the discharge electrodes at an adjustable frequency;
b) circulating the gas sample through the plasma chamber;
c) generating a plasma from the carrier gas in the plasma chamber using the plasma-generating mechanism;
d) continuously measuring an optical emission from the plasma and adjusting the frequency of the discharge driving signal in real time to maintain the measured optical emission constant;
e) introducing time-separated peaks of said impurities in the flow of carrier gas; and
f) monitoring the frequency of the discharge driving signal and detecting the gas species through variations in said frequency.

The monitoring of step f) may involve converting said frequency to a voltage value, and optionally zeroing the voltage value prior to the introducing of the time-separated peaks.

In some implementations, the optical emissions measured at step d) may consist in a spectral line of the gas species to be measured, or in broad spectrum light emitted by the plasma.

In accordance with one more aspect, there is provided a method of measuring a gas species in a gas sample, comprising:
a) providing a plasma-based optical emission gas detector comprising a plasma chamber and a plasma-generating mechanism configured to apply a plasma-generating field across the plasma chamber;
b) circulating the gas sample through the plasma chamber;
c) generating a plasma from the gas sample in the plasma chamber using the plasma-generating mechanism;
d) doping the gas sample in the plasma chamber with at least one dopant interacting with said gas species within the plasma; and
e) measuring optical emissions affected by said interacting of the at least one dopant with the gas species.

In some implementations, the optical emissions measured at step e) may correspond to at least one spectral line characteristic of the at least one dopant, to at least one spectral line characteristic of the gas species that are affected by the interacting of said gas species with the at least one dopant and/or to at least one spectral line characteristic of a gas constituent by-product of the interacting of the at least one dopant with the gas species to be detected.

According to another aspect, there is also provided a plasma doping module for a plasma-based optical emission gas detector comprising a plasma chamber traversed by a gas flow path allowing a flow of a gas sample through the plasma chamber.

The plasma doping module includes an injection tubing connected to the plasma chamber and carrying the flow of the gas sample to the plasma chamber. An electrically conductive tube extends within the injection tubing, the electrically conductive tube having an inlet projecting out of the injection tubing and connectable to a dopant source to receive a flow of dopant gas therefrom, and an outlet projecting within the plasma chamber to output said flow of dopant gas into said plasma chamber. The plasma doping module further includes a pre-ionisation electrode in contact with the injection tubing coextensively with the flow of dopant gas, and a pre-ionisation voltage source connected to the electrically conductive tube and to the pre-ionisation electrode to apply a voltage therebetween, thereby pre-ionising the flow of dopant gas.

In some implementations, the pre-ionisation electrode is a tubular electrode surrounding a segment of the injection tubing.

In some implementations, the plasma doping module further comprises a frit or a metallic porous disc at the outlet of the electrically conductive tube.

In some implementations, the pre-ionisation voltage source generates an AC or a pulsed pre-ionisation driving signal.

Other features and aspects of the invention will be better understood upon reading of embodiments thereof with reference to the appended drawings.

DETAILED DESCRIPTION

In accordance with embodiments, there are provided plasma-based optical emission detectors using optical spectroscopic techniques for detecting, measuring and/or analysing the constituents of gas samples.

Plasma-based detectors according to various embodiments may be of particular use for chromatography applications. Chromatography is a technical field where constituents of a gas sample are separated in order to be individually analysed. In some implementations, therefore, the plasma-based detectors described herein may be used to detect and analyse the components of a gas sample outputted by a chromatography column. Typically, the gas stream outputted by a chromatography column includes one or more impurities or species to be detected carried by a carrier gas, different species being outputted at different moments in time. The species to be detected may for example be hydrogen ($H_2$), argon (Ar), oxygen ($O_2$), methane ($CH_4$), carbon monoxide (CO), carbon dioxide $CO_2$), water ($H_2O$), hydrocarbons, BTEX compounds, etc. Different types of carrier gases may also be selected depending on the application and the particularities of a given chromatography system. Typical carrier gases include argon (Ar), helium (He), nitrogen ($N_2$), hydrogen ($H_2$) and oxygen ($O_2$).

It will however be readily understood that in other implementations the plasma-based detectors described herein may be of use in other technical fields, such as for example gas purification systems, gas leak detection systems, or online gas analysers without chromatographic separation.

In accordance with various implementations, the plasma-based detector described herein may be provided with one or more features allowing its use for different applications and in different operating conditions. Combining at least some of these features can therefore provide a "multimode" device which can be used in conjunction with different carrier gases, different impurities, different sample flow parameters, etc. Various such features are explained in the description below.

Plasma Generation and Control

Figure 1:
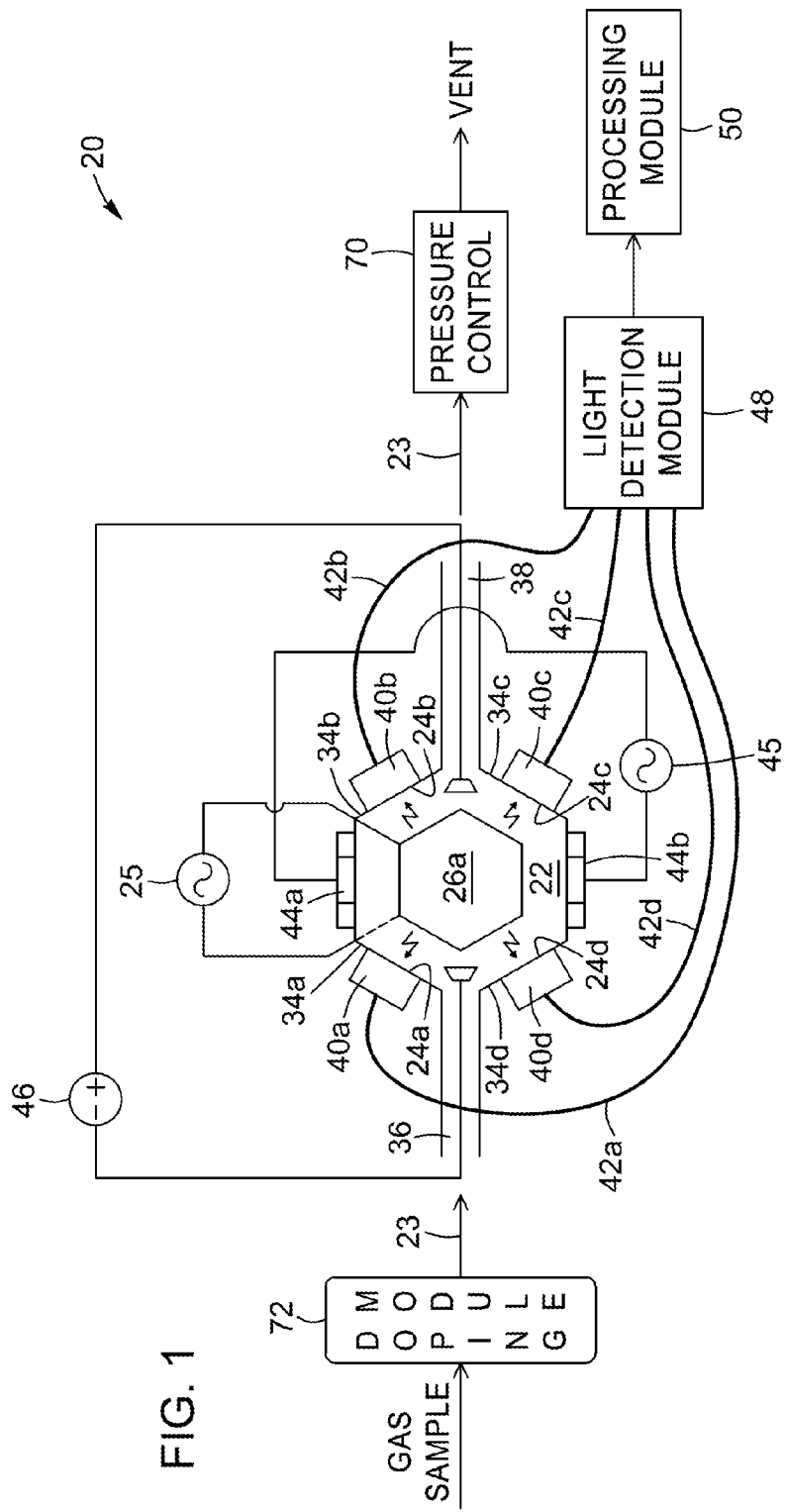
FIG. 1 is a schematic representation of the components of a plasma-based optical emission gas detector according to an embodiment.
Figure 3:
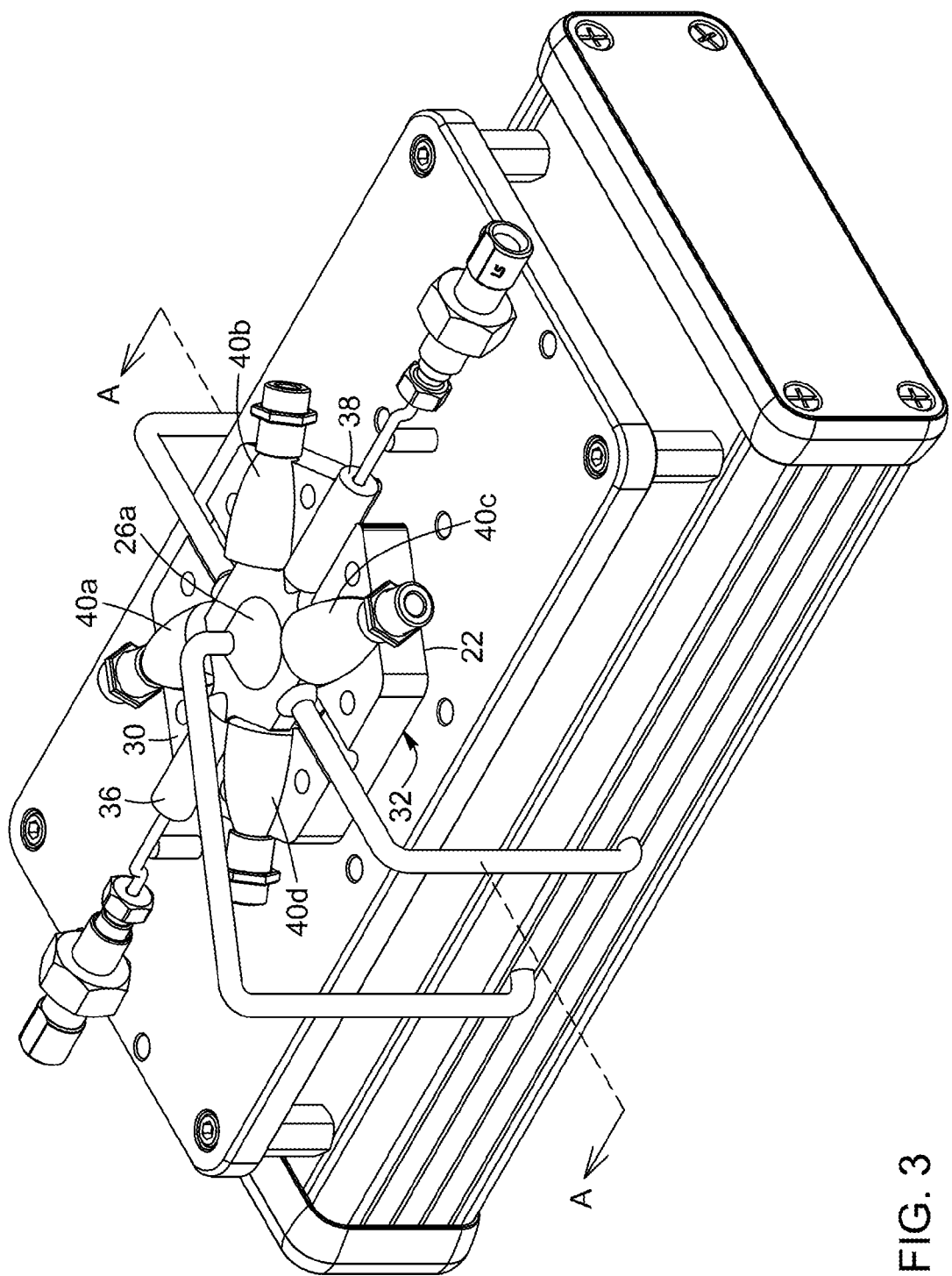
FIG. 3 is a perspective elevation view of a plasma-based optical emission gas detector according to an embodiment.
Figure 3A:
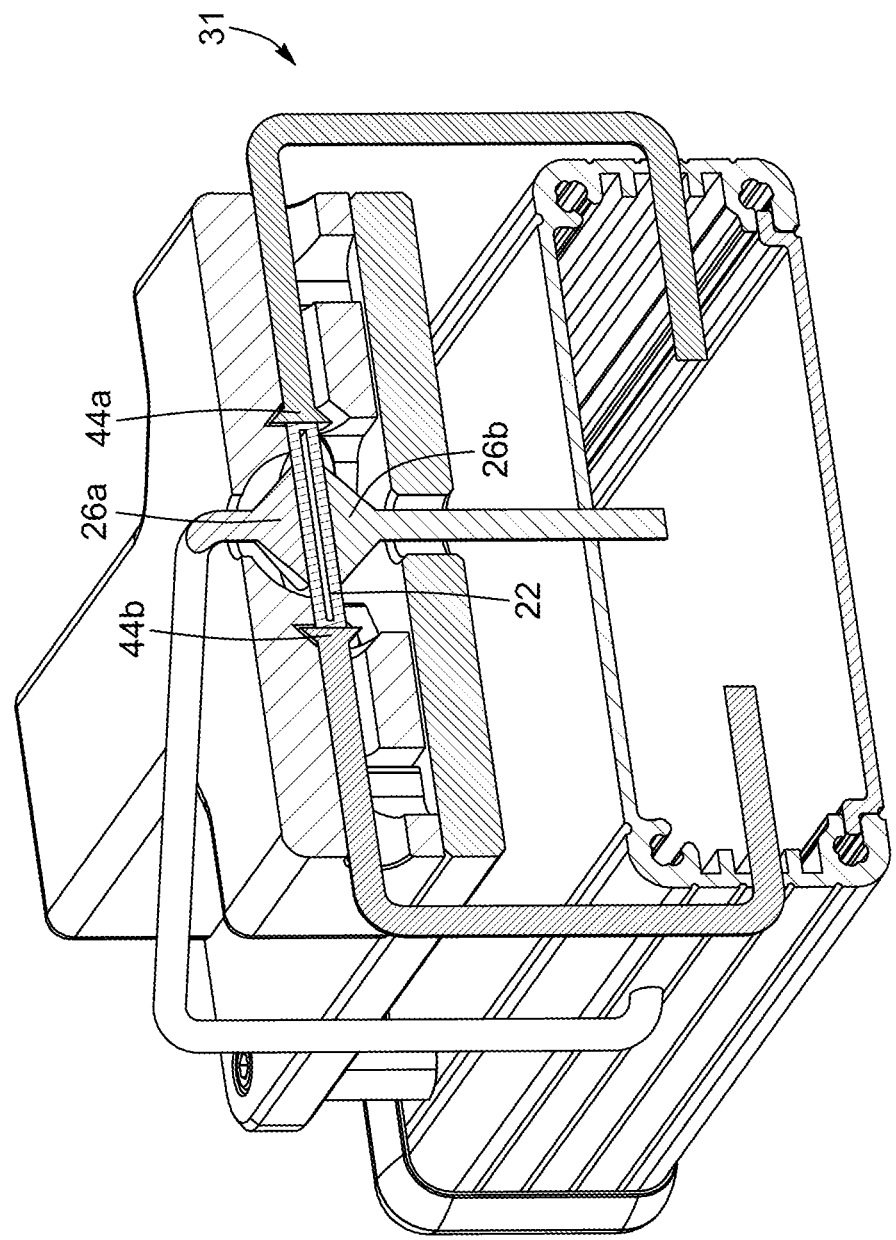
FIG. 3A is a cross-section along lines A-A of FIG. 3.

Referring to FIGS. 1, 3 and 3A, there is shown a plasma-based detector 20 according to one implementation. The plasma-based detector 20 first includes a plasma chamber 22 traversed by a gas flow path 23 allowing a flow of a gas sample through the plasma chamber 22. In the illustrated embodiment, the plasma-based detector 22 includes a gas inlet 36 and a gas outlet 38, allowing circulation of the gas sample to be analysed through the detector along the gas flow path 23. The plasma chamber 22 may be embodied by any enclosure suitable to host a plasma and allow optical emissions to be transmitted out of the plasma chamber 22. In some embodiments, the plasma chamber 22 may be entirely made of quartz, which is a material transparent to a broad spectral range, including UV radiation. In other embodiments the plasma chamber may be made of another transparent or non-transparent material such as glass-type materials including ceramics, borosilicate glasses or semi-crystalline polymers such as for example PEEK (polyether ether ketone). The plasma chamber 22 may be provided with one of more windows 24a to 24d allowing optical emissions from the plasma to exit the plasma chamber 22 therethrough, within a spectral range of interest. Suitable materials for such windows 24a to 24d may for example include quartz, calcium fluoride ($CaF_2$) or magnesium fluoride ($MgF_2$) which can be particularly transparent to UV radiation, zinc selenide (ZnSe) materials for measurements in the infrared spectrum, etc. In other implementations, one or more of the windows 24a to 24d may be made or fluorescent glass. Such embodiment may for example be useful for applications where the spectral lines of interest are in the UV range and it is desirable to maximize sensitivity, while reducing noise and drift. For example, the fluorescent glass may get excited by UV radiation and generate emission in the visible range upon de-excitation.

In the illustrated embodiment, the plasma chamber 22 is shown as having four (4) windows 24a, 24b, 24c and 24d. Other configurations may of course be envisioned without departing from the scope of the invention. It will be readily understood that different windows 24a to 24d of a given plasma chamber 22 need not be made of a same material. As a matter of fact, in some embodiments different windows may be fabricated using materials having different spectral transmission properties so that each window may be of particular use for detecting optical emissions within a dedicated spectral range.

Figure 4:
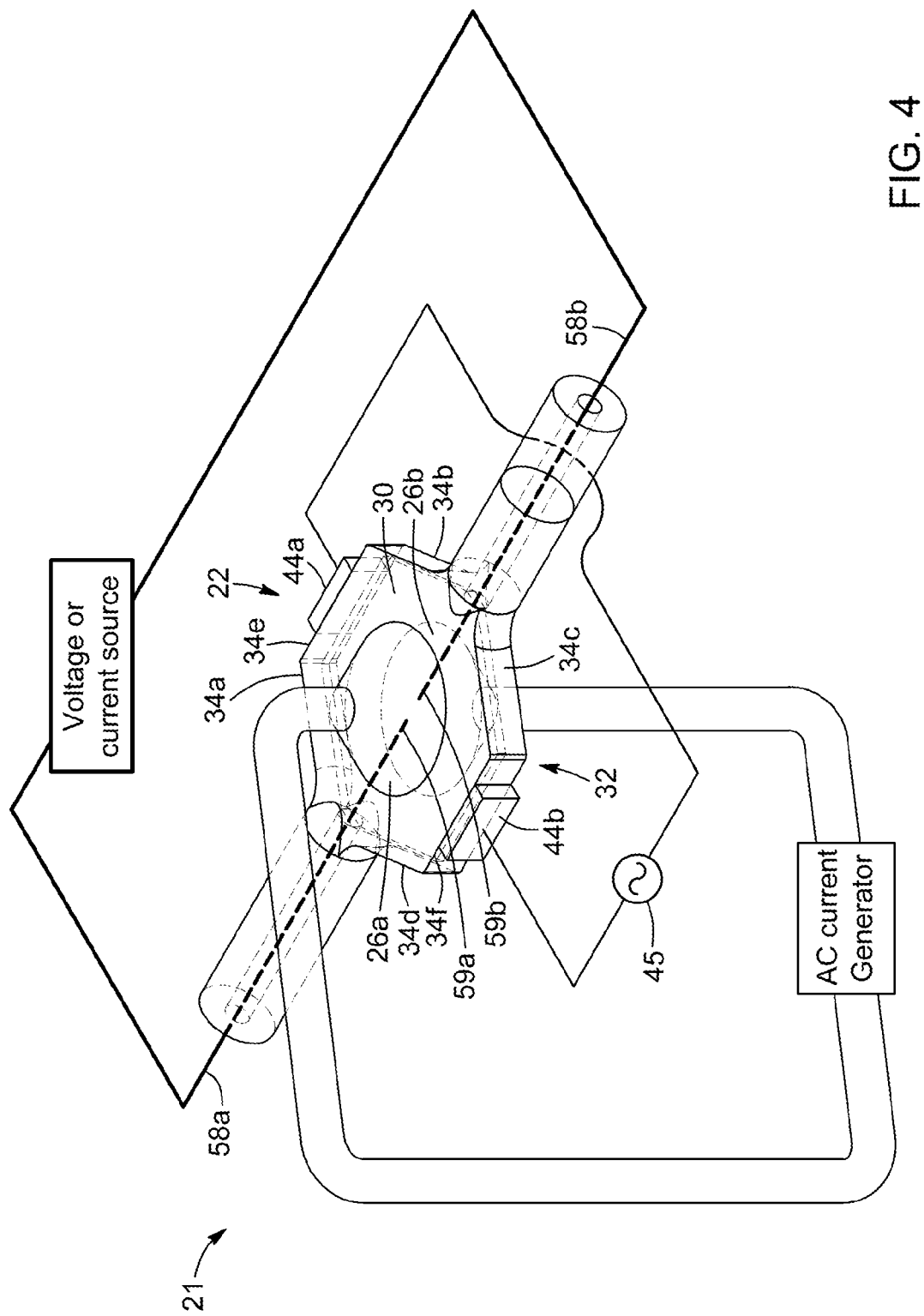
FIG. 4 is a view is partial transparency of the plasma chamber of the plasma-based optical emission detector of FIG. 3, provided with electron-injecting electrodes according to one variant.

Referring to FIG. 4, the plasma-based detector 20 further includes a plasma-generating mechanism 21 configured to apply a plasma-generating field across the plasma chamber 22 intersecting the gas flow path 23, so as to generate a plasma from the gas sample. Preferably, the plasma-generating mechanism relies on a Dielectric Barrier Discharge (DBD).

DBD Plasma-Generating Process

Figure 2:
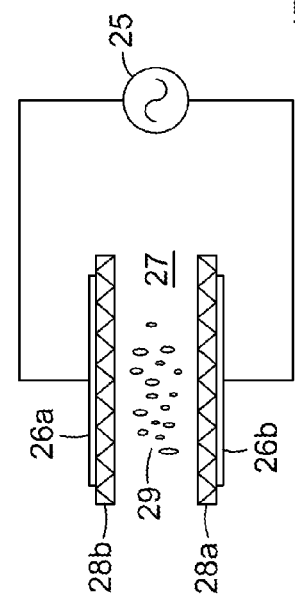
FIG. 2 (PRIOR ART) is a schematic representation of a Dielectric Barrier Discharge plasma-generating configuration.

An example of a DBD configuration is schematically illustrated in FIG. 2. DBD involves the use of a pair of discharge electrodes 26a, 26b separated by a discharge gap 27, in which is provided one or more insulating dielectric barrier 28a, 28b. A discharge gas 29 suitable to breakdown under an applied electrical field is provided in the discharge gap 27. An alternating current generator 25 provides a high voltage alternating current (AC) driving signal to the discharge electrodes 26a, 26b. As this AC discharge driving signal is applied to the discharge electrodes 26a, 26b, the dielectric material of the dielectric barrier 28a, 28b (for example quartz) polarizes and induces a plasma-generating electrical field in the discharge gap 27, leading to the breakdown of the discharge gas 29 and the creation of a plasma medium in the discharge gap 27. This high ignition potential produces ionisation of the gas and the resulting electrons and ions travel towards the opposite polarity discharge electrodes 26a, 26b, charging the respective discharge electrodes 26a, 26b positively and negatively, producing a decrease of the applied electrical potential that in turn conducts to extinguish the plasma. The presence of the dielectric barrier limits the average current density in the plasma. It also isolates the discharge metal electrodes from the plasma, avoiding sputtering or erosion. When the discharge driving signal polarity is reversed, the applied potential and the memory potential due to charge accumulation on the surface of the dielectric barriers 28a, 28b are added and the discharge starts again. The potential required to sustain the plasma is therefore lower than the initially required potential for ignition.

The plasma-generating process therefore begins with the applying of a plasma-generating electrical field across the plasma chamber 22 that transfers enough energy to free electrons in the discharge gap 27 so that they ionise particles of the gas sample through collisions. From that point an avalanche occurs and other ionisation mechanism can take place. Such mechanisms include, but not limited to:

Direct ionization by electron impact. This mechanism involves the ionization of neutral and previously unexcited atoms, radicals, or molecules by an electron whose energy is high enough to provide the ionization act in one collision. These processes can be dominant in cold or non-thermal discharges, where electrical fields and therefore electron energies are quite high, but where the excitation level of neutral species is relatively moderate;

Ionization by collision of heavy particles. This takes place during ion-molecule or ion-atom collisions, as well as in collisions of electronically or vibrationally excited species, when the total energy of the collision partners exceeds the ionization potential. The chemical energy of colliding neutral species can also contribute to ionization in so-called associative ionization processes;

Photo-ionization refers to the excitation of neutrals by photons, which result in the formation of an electron-ion pair. Photo-ionization can be dominant in thermal plasmas but may also play a significant role in regard to the mechanisms of propagation of non-thermal discharges;

Surface ionization (electron emission). This process is provided by electron, ion, and photon collisions with different surfaces or simply by surface heating;

Penning ionization is a two (2) steps ionisation process involving a gas mixture. For example, the gas detector may operate with a doping gas such as He or Ar added to the detector entrance and mixed to the flow of carrier gas. Direct ionisation by electron impact first provides excited atoms. These electronically excited atoms interact with a target molecule, the collision resulting in the ionization of the molecule yielding a cation, an electron, and a neutral gas molecule, in the ground state.

In the context of plasma-based gas detectors, the discharge gas 29 is embodiment by the gas sample passing through the plasma chamber along the gas flow path 23. As mentioned above, the gas sample may for example be embodied by solute from a gas chromatography system, or other gas samples whose composition is to be analysed. Typically, the gas sample includes a carrier gas of a known nature (such as for example He, Ar, $N_2$, $CO_2$, $H_2$, $O_2$, etc), in which are present impurities to be identified and/or measured. As mentioned above, the impurities may for example be embodied by hydrocarbons, $H_2$, Ar, $O_2$, $CH_4$, CO, $CO_2$, $H_2O$, BTEX compounds, and the like.

Exemplary Plasma-Generating Mechanism

Referring back to FIGS. 1 and 4, in the illustrated implementation the plasma-generating mechanism 21 therefore includes a pair of discharge electrodes 26a, 26b extending parallelly on opposite sides of the plasma chamber 22 and separated by a discharge gap embodied by the inner volume of the plasma chamber 22. The plasma-generating mechanism 21 further includes a pair of insulating dielectric barriers each extending within the discharge gap along a corresponding one of the discharge electrodes 26a, 26b. In some implementations, one or more walls of the plasma chamber 22 may act as the dielectric barrier or barriers of the DBD process. In the illustrated embodiment, there is shown an example of a plasma chamber 22 having a flat configuration defined by hexagonal top and bottom walls 30 and 32 and side walls 34a to 34f. The discharge electrodes 26a, 26b extend along and in direct contact with the top and bottom walls 30 and 32. In one embodiment, each discharge electrode 26a, 26b may be embodied by a layer of conductive compound extending along an exterior surface of the corresponding wall 30, 32 of the plasma chamber 22. The top and bottom walls 30 and 32 may be made of an insulating material such as quartz. The illustrated plasma-generating mechanism therefore provides a planar DBD configuration where the top and bottom walls 30 and 32 of the plasma chamber 22 act as the dielectric barriers that extend in direct contact with each electrode 26a, 26b, embodying the configuration schematized in FIG. 2. It will however be understood that different shapes and configurations for the plasma chamber 22, dielectric barriers and discharge electrodes 26a, 26b can easily be envisioned without departing from the scope of the invention.

The plasma-generating mechanism 21 further includes an alternating current generator 25 providing an alternating discharge driving signal to the discharge electrodes 26a, 26b, thereby creating a voltage across the plasma chamber 22 having a peak voltage value and an oscillating frequency determined by the alternating discharge driving signal. One skilled in the art will readily understand that the peak voltage and frequency of the alternating current generated by the alternating current generator 25 is preferably selected in view of the nature of the discharge gas and operating conditions in the plasma chamber 22, in order to favor breakdown of the discharge gas and generation of a plasma suitable for a target application. The peak voltage required to create a discharge depends on several application-specific factors, such as the ease of ionisation of the discharge gas. For example, at atmospheric pressure helium requires a voltage of about 2 kV peak to peak, whereas argon requires about 4 kV and $N_2$ up to 10 kV. Operating at lower pressure can significantly decrease the required voltage to achieve ionisation. The waveshape of the alternating discharge driving signal may for example be square or sinusoidal. In one embodiment, the use of a medium frequency sinusoidal shape driving signal, for example under 1 MHz, has been found to reduce spurious harmonic generate by the system. Finally, the frequency of the alternating discharge driving signal may also be used as a parameter to control and/or improve the plasma-generating process. As will be readily understood by one skilled in the art, variations in the frequency of the discharge driving signal will directly impact the intensity of the plasma, and therefore the intensity of the optical emissions from the plasma. Indeed, the higher the excitation frequency, the stronger the resulting plasma-generating field, and therefore the greater the movement of the electron within the plasma chamber back and forth between the discharge electrodes. This parameter therefore has a direct on the strength of the light emitted from the plasma, and therefore increases the intensity of the detected signal for a same quantity of impurities in the flow of the gas sample.

As will be readily understood by one skilled in the art, the plasma generated through DBD configurations such as described herein typically constitutes a "soft plasma" maintained in a non-thermal equilibrium regime. In such plasma, the momentum transferred between electrons and heavy particles such as ions and neutral particles is not efficient, and the power coupled to the plasma favors electrons. The electron temperature ($T_e$) is therefore considerably higher than the temperatures associated with ion ($T_i$) and neutral particles ($T_n$). In other words, the electrical energy coupled into the plasma is mainly transferred to energetic electrons, while the neutral gas and ions remain close to ambient temperature and exploits the more appropriate behaviour, characteristic or phenomenon of the plasma discharge.

It will be readily understood that the properties of the generated plasma depend on the nature of the gas being ionised to generate the discharge. In chromatographic application, the carrier gas used in the chromatographic process typically dominates the plasma-generation process. Typical carrier gas used such as argon or helium can provide a usable plasma at atmospheric or high pressure. Argon generally creates a "streamer"-type discharge, whereas Helium results in a "glow"-type discharge. Both types of discharge may be used in the context of embodiments of the present invention. Furthermore, as will be explained below, in some implementations the generated plasma may be based on other gases, including gases more difficulty ionised at atmospheric pressure, such as $N_2$, $H_2$, $O_2$ and the like.

Plasma Localizing Field

One of the drawbacks of a DBD is that there can be a substantial displacement or movement of the plasma within the plasma chamber during the detection process. Such a displacement can for example be present under particular operating conditions such as sudden flow change, high pressure, a high level of impurities inside the plasma chamber or when the plasma operating power is low. The type of discharge gas used to generate the plasma can also influence the spatial stability of the generated discharge. Under such conditions, the discharge may exhibit what may look, even to the naked eye, like turbulence.

The movement of the plasma within the plasma chamber 22 can have a significant impact on the process of detecting and analysing the generated radiation. Over the course of a discharge, movements of the plasma within the plasma chamber 22 can displace the plasma in and out of alignment with one or more of the windows 24a to 24d, affecting the proportion of the generated radiation collected by the corresponding light collecting assembly. This can create substantial noise in the intensity of the signals received and processed by the processing module.

In accordance with one aspect, plasma stability may be improved by applying a localizing electrostatic, magnetic or electromagnetic field, preferably transversally to the plasma-generating field. As the plasma within the plasma chamber is a charged medium, it can be extended, compressed or moved under the influence of such fields.

Referring again to FIGS. 1, 3 and 3A, in accordance with one implementation, the plasma-based optical emission detector 20 includes a plasma-localizing mechanism 31 configured to apply a plasma-localizing field across the plasma chamber 22, and positioned such that the plasma-localizing field localizes the plasma within the plasma chamber 22 in alignment with the optical window or windows 24a to 24d.

In some embodiments, the plasma-localizing mechanism 31 includes a pair of localizing electrodes 44a, 44b, extending parallelly on opposite sides of the plasma chamber 22. The plasma-localizing field of these embodiments is therefore an electrical field.

In the illustrated variant, there is shown an example of electrode configuration according to one implementation, in which the plasma-localizing field is applied transversally to the plasma-generating field. In this case the top wall 30 and bottom wall 32 of the plasma chamber define a pair of opposite first walls, associated with the plasma-generating mechanism 21. In the illustrated variant the plasma chamber 22 has an hexagonal configuration, a pair of opposite sides walls (34e and 34f) defining second walls associated with the plasma-localizing mechanism whereas the remaining side walls (34a to 34d) are associated with windows 24a to 24d.

The localizing electrodes 44a, 44b are disposed along opposite walls 34e and 34f of the plasma chamber 22. The localizing electrodes may for example be embodied by metallic electrodes affixed to the walls 34e, 34f of the plasma chamber 22 through an electrically conductive adhesive, or by a layer of conductive compound extending along an exterior surface of the corresponding side walls 34e, 34f. The localizing electrodes are electrically connected to a high power supply 45. In one example, the power supply 45 is configured to apply a DC localizing drive signal on the localizing electrodes 44a, 44b, creating an electrostatic field between them. The electrostatic field guides the plasma up or down within the plasma chamber 22, and its strength can be adjusted so that the plasma is in line with one or more of the windows 24a to 24d. In one variant, the power supply 45 may be configured to apply a localizing drive signal on the localizing electrodes 44a, 44b including both a DC component and an AC component. Advantageously, the AC component of the localizing drive signal may be synchronized with the discharge driving signal. The AC component may be user-triggered as required.

Controlling and managing the electrical field between the localizing electrodes may provide an improved control of the stability and position of the plasma. Depending on the polarity of the plasma, the electrodes may be both negative, both positive or one electrode negative and the other positive. As the plasma within the chamber 22 is a charged medium, its position will be controlled by the electrical field between the localising electrodes 44a, 44b, helping maintain its spatial distribution. This in turn stabilizes the alignment of the plasma with the windows 24a to 24d, ensuring the stability of the light collection through these windows. In other embodiments, the plasma-localizing mechanism may include a pair of electromagnets (not shown) extending parallelly on opposite sides of the plasma chamber 22, in which case the plasma-localizing field is embodied by a magnetic field.

It will be readily understood that the characteristics of the field created between the localizing electrodes or magnets can be used as control parameters for the resulting position and distribution of the plasma within the plasma chamber. This feature can be combined with knowledge of the composition of the gas to be analysed to optimize detection of each impurity therein. The localizing driving signal may be controllable to align the plasma with a selected one of the windows 24a to 24d in synchronicity with the passage of a predetermined impurity peak in the gas sample along the gas flow path. For example, the solute stream outputted by a chromatography column separates in time the impurities present in the carrier gas according to a known sequence. In one example, each window of the plasma chamber may be dedicated to one impurity type, and the field generated by the localizing electrodes may be controlled in real time to align the plasma discharge with the appropriate window upon arrival of a given impurity peak. Each is therefore associated with optical emissions in a different spectral range, and the plasma-localizing mechanism is further configured to adapt the plasma-localizing field to align the plasma with a selected one of these windows in synchronization with a passage of a gas species emitting in the corresponding spectral range through the plasma chamber.

Figure 4A:
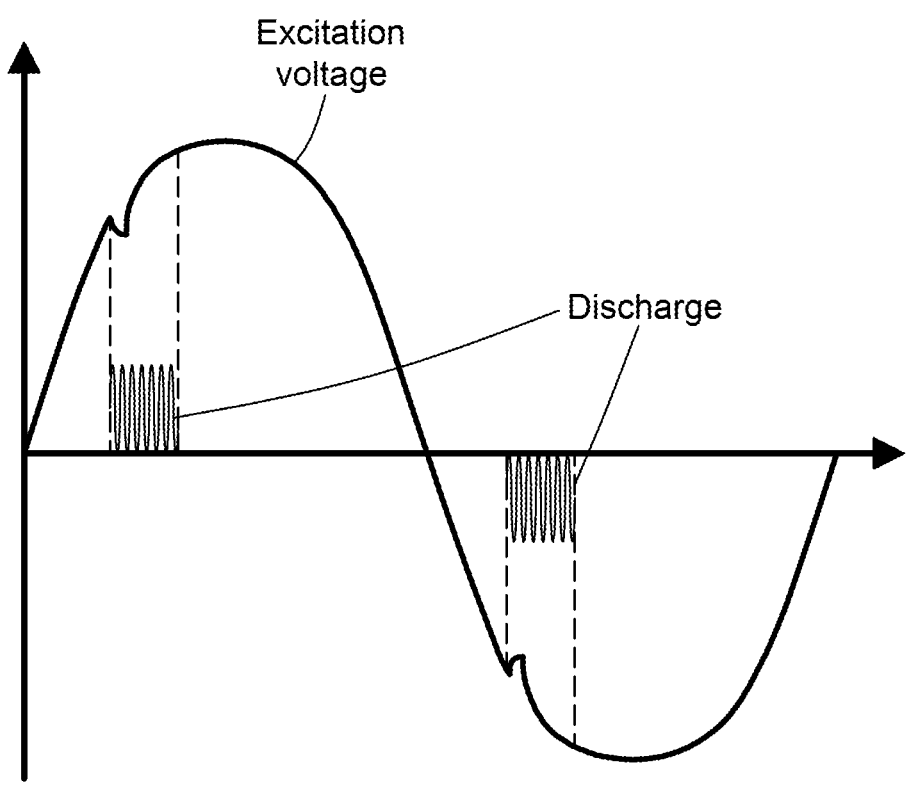
FIG. 4A is a graph showing an example of the waveshape of a discharge driving signal according to one embodiment.

In some embodiments, as mentioned above, the localizing driving signal may be synchronized with the discharge driving signal. Such that transversal electrostatic, magnetic or electromagnetic plasma-localizing field may be controlled to define a series of pulses in coordination with the plasma-generating field. In some implementations, the plasma is not embodied by a continuous discharge, but is instead composed of a series of self-extinguishing discharges emitting light in the form of light pulses. An example of a typical waveform of the discharge driving signal applied to the discharge electrodes and the resulting light emissions created by the discharge is shown in FIG. 4A. This phenomenon is the result of charge build-up on the walls of the plasma chamber. Advantageously, in some embodiments, by superimposing a pulsed voltage waveform to the voltage signal applied to the localizing electrodes to establish the electrostatic field that positions the plasma, a more uniform or stable discharge may obtained. The pulse train reduces the wall charge build-up by causing charges to drift away. It has been found that even a partial drifting effect can greatly improve the stability of the resulting plasma.

Electron Injection

Gas chromatographic systems used for bulk gas measurements typically use helium or argon as carrier gas. Generally speaking, it is relatively easy to start and maintain a plasma discharge in argon or helium, and this, at atmospheric or even higher pressure. Therefore, igniting a plasma when operating with such gases usually involves only routine considerations for one skilled in the art. Typically, this involves applying an initially high voltage to the discharge electrodes and when the discharge is ignited, the voltage is decreased in order to maintain a stable plasma. Higher continuous excitation voltage may lead to instability. In some variants, photon assisted starting discharge systems can also be used, as is well known in the art, especially in conjunction with argon or helium as carrier gases. This concept consists in irradiating the discharge gap with photons in the UV range, releasing electrons from the discharge gas through photo-ionisation. The released electrons are accelerated by the excitation field, reducing start up time and voltage. While this approach improves efficiency when working with argon and helium, it is however not the case when working with gases more difficulty ionised at atmospheric pressure, such as $N_2$, $H_2$ and $O_2$, unless a very high intensity beam is used.

When using $N_2$, $O_2$ or $H_2$ as carrier gas, an intense initial voltage is required to start the plasma and once it has started, the discharge is not typically stable and tends to shut down by itself if there is a sudden flow change or pressure upset in the plasma chamber.

In accordance with one aspect, operation of the plasma-based detector described herein using hard to ionise carrier gases may be facilitated by providing a mechanism for injecting free electrons in the plasma chamber. Indeed, it is believed that the lack of free electrons in hard to ionise gases is a factor affecting the stability of the discharge.

Referring to FIGS. 1 and 4, in some implementations the plasma based detector 20 may include a pair of electron-injecting electrodes 58a, 58b, serving this purpose. Each electron-injecting electrode has an extremity 59a, 59b projecting within the plasma region, that is, the volume of the plasma chamber 22 occupied by the plasma. The extremities 59a, 59b of the electron-injecting electrodes 58a, 58b project within the plasma chamber 22 from opposite sides thereof. In the illustrated embodiments, the electron-injecting electrodes 58a, 58b are provided through the gas inlet 36 and gas outlet 38, respectively. The electron-injecting electrodes may each have a needle or a flat-tip shape, although other shapes may also be considered. In use, a voltage is applied to the electron-injecting electrodes 58a, 58b. In the illustrated embodiment of FIG. 1 the plasma-localizing mechanism is shown as including a DC voltage source 46, although in other variants an AC voltage source or a current source configuration could also be used.

It will be readily understood that although presented herein in the context of optical emission gas detectors, the use of electron-injecting electrodes such as described herein may also be useful to other types of plasma-based detectors.

Pressure Control Mechanism

Figure 5:
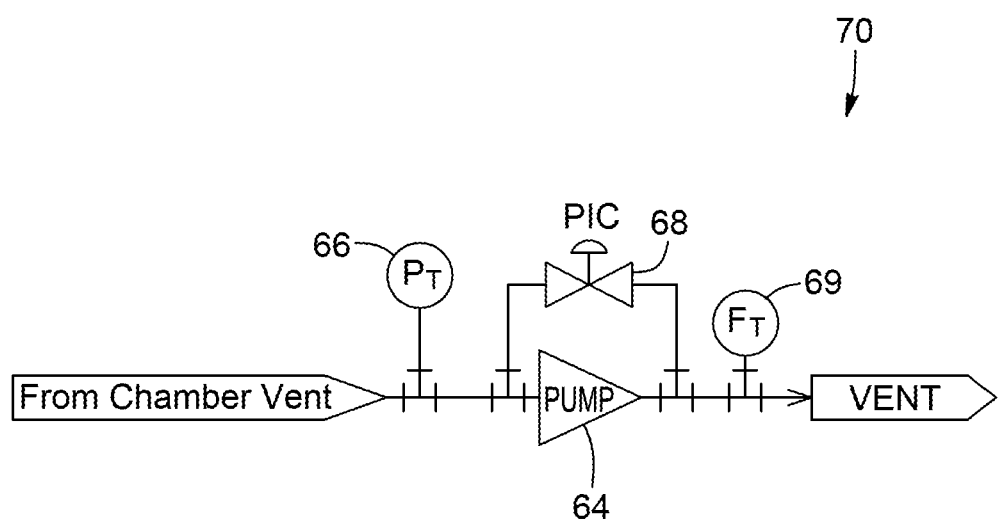
FIG. 5 is a schematized representation of a pressure control mechanism for use in a plasma-based optical emission detector according to one variant.

Referring to FIGS. 1 and 5, in one variant the plasma-based detector 20 may also include a pressure control mechanism 70 configured to control a pressure within the plasma chamber 22. The pressure control mechanism 70 is preferably provided along the gas flow path 23 downstream the plasma chamber 22, and is for example connected to the vent or outlet 38 of the plasma chamber 22 through stainless steel or other suitable tubing. In the illustrated embodiment the pressure control mechanism 70 includes a pump 64 (for example a twin head diaphragm pump) and a control by-pass valve 68 installed around the pump 64. The pressure in the plasma chamber 22 can be controlled by controlling the operation of the by-pass valve 68. The illustrated pressure control mechanism 70 further includes a pressure controller 66, for example an absolute pressure transducer connected to the gas outlet 38. A flow sensor 69 may be provided at the discharge of the pump 64. Signals from the pressure controller 66 and flow sensor 69 may be used as feedback information in the operation of the plasma-based detector. Of course, other configurations for the pressure control mechanism 70 may be envisioned without departing from the scope of the invention.

The pressure control mechanism can be used to control the pressure within the plasma chamber in a variety of contexts.

In one implementation, the pressure control mechanism 70 may be used in conjunction with the electron-injecting electrodes 58a, 58b in carrying out a method for generating a plasma in a plasma chamber of a plasma-based gas detector. This method may for example include the following steps:

a) circulating a flow of a gas sample through the plasma chamber 22. As mentioned above, the gas sample preferably includes carrier gas made of a hard-to-ionize gas species such as $N_2$, $O_2$ or $H_2$.

b) controlling a pressure inside the plasma chamber to a sub-atmospheric level. This is preferably accomplished through a pressure control mechanism such as mentioned above.

c) applying a plasma-generating field across the plasma chamber intersecting the flow of gas sample so as to generate a plasma from the gas sample. Preferably, a high voltage is applied to the discharge electrodes 26a, 26b in order to achieve a discharge from the carrier gas.

d) putting respective extremities of a pair of electron-injecting electrodes 58a, 58b in contact with the plasma. Preferably, the electron-injecting electrodes are provide within the plasma chamber 22 through the gas inlet 36 and gas outlet 38, and project sufficiently far within the plasma chamber 22 such that at least their extremities 29a, 29b extend within the plasma region.

e) applying a voltage on the electron-injecting electrode 58a, 58b such that free electrons are injected within the plasma chamber 22, increasing the number of free electrons within the plasma region. As plasma is electrically conductive, electrons are moved from the negative electron-injecting electrode in the direction of the positive one, establishing a current between the electron-injecting electrodes 58a, 58b and across the plasma chamber.

Since the operating pressure is sub-atmospheric, the mean free path of electrons is greater than it would otherwise be at atmospheric pressure. Under the excitation field generated by the discharge electrodes 26a, 26b, electrons will gain more speed than at atmospheric pressure. The generated collisions are therefore more energetic, enabling the generation of stable plasma when using gases difficult to ionise. Once the discharge is ignited, it may be possible to increase the pressure slightly while conserving the discharge. Another benefit of operating under low pressure is that impurities having a higher excitation potential than the carrier gas are excited, and can be more easily detected by emission spectroscopy.

Since the plasma is electrically conductive, the voltage applied on the electron injection electrodes 58a, 58b can be low, for example of the order of a few hundred volts, and electrode sputtering effects can be avoided or mitigated.

In accordance with another implementation, the provision of a pressure control mechanism such as described above shown in FIG. 5, or the like, may also be of use to provide different operation modes in view of the volume and flow of the gas sample to be analysed. The plasma operating pressure could be changed in real time, or simply maintained at any particular value that optimizes the system for particular operating conditions.

In accordance with some embodiments, a method of detecting a gas species in a gas sample using a plasma-based optical emission gas detector having a plasma chamber and a pressure control mechanism is provided. The pressure control mechanism is operable to control the pressure in the plasma chamber over a continuous pressure range. One skilled in the art will understand that the continuous pressure range may substantially extend between vacuum pressure and atmospheric pressure, or may span a subset of this range.

The method next includes selecting a pressure setting based on one or more sample characteristics associated with the gas sample.

The sample characteristics may for example include the volume of the gas sample flowing through the plasma chamber.

For several standard gas chromatographic applications, operating at atmospheric pressure works very well. For example, working with bulk or permanent gases outputted at PPM levels from packed columns of ¹⁄₁₆" or ⅛" with carrier flow ranging from 5 to 30 sccm can provide easily detectable emission lines with available devices. In such a context the volume of the plasma chamber does not significantly affect the intensity of the emission peaks and does not significantly "dilute" the impurity peak. This is however not the case when working with smaller "capillary"-type columns through which gas flow is below 1 sccm, and the volume occupied by the gas sample is very small. In such a situation, the residence time of the sample inside the detector may become too long, causing peak broadening. Furthermore, since the sample loop size is very small in capillary chromatography, the sample "slug" allowed to flow into the detector will suddenly be diluted into the internal volume or space of the detector. It results in sample dilution, reducing system sensitivity.

Attempts have been made in the past to use a dielectric barrier discharge (DBD) with capillary columns. The volume of the plasma chamber in these attempts has been made small to fit capillary column chromatography. However, the sensitivity of the resulting detector suffered since the corresponding discharge size was very small. Furthermore, for practical reasons, it is not always possible to reduce the size or volume of the plasma chamber below a certain value, since the size of the plasma discharge would then become too small and the light intensity too weak. In other words, the optimal chamber volume must take into account discharge and optical performance requirements.

For such situations, amongst others, it can be desirable to operate the plasma chamber at reduced pressure. By reducing the operating pressure, the residence time is dramatically decreased and flow velocity increased. Varying the pressure allows to "tune" the internal volume of the plasma chamber to optimize the emission peak shape. The volume of gas at any time inside the plasma chamber could be much lower than the sample volume size. This maximizes sensitivity, since there is no dilution phenomenon inside the cell. Low pressure operation reduces detector baseline and increases impurity emission line intensity since the electron mean free path increase; another benefit when working with capillary chromatography.

In other implementations, the sample characteristic may include an excitation potential of the gas species.

By operating the plasma at reduced atmospheric pressure, the mean free path of the electrons in the plasma chamber (resulting from the collisions between molecules in the gas sample under the plasma-generating field and/or from the electron-injecting electrodes) is increased. The kinetic energy of these electrons is consequently also increased and more energy is available for the excitation/ionization of neutral atoms and molecules. As a result, operating at lower pressure reduces the quenching of a target impurity, especially for impurity species having a higher excitation/ionization potential than the gas background or carrier gas, such as for example neon impurities in an argon background.

Quenching occur when an excited molecule or atom is de-excited without any photon emission, typically during collision and energy transfer to a colliding particle. Reducing plasma pressure allows the low population of the target impurity to be de-excited by the emission mechanism before colliding with other particles or the wall of the plasma chamber.

Once a desired pressure setting has been set, the method includes circulating a flow of the gas sample through the plasma chamber, and then generating a plasma from the gas sample in the plasma chamber, as explained above. The method then involves controlling the pressure control mechanism to maintain the pressure in the plasma chamber at the selected pressure setting. This may be achieved by using a feedback loop, for example measuring the pressure of the gas sample downstream the plasma chamber and operating a pump in the pressure control mechanism if view of the measured pressure. The gas species can then be detected by measuring optical emissions from the plasma indicative of their presence. This measuring can be performed at one or more wavelengths characteristic of the gas species, as explained above. In another variant, the overall intensity of the light from the plasma may be monitored to indicate the presence of impurity without specific species identification.

Plasma Doping Module

Referring to FIGS. 1 and 6A to 6C, the plasma-based optical emission gas detector 20 may further include a plasma doping module 72 configured to inject at least one dopant species to the gas sample flowing through the plasma chamber 22.

Figure 6A:
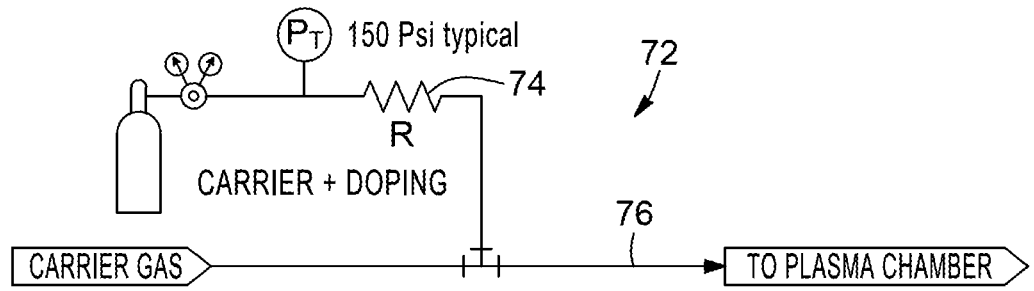
FIGS. 6A to 6D are schematized representations of a doping module for use in a plasma-based optical emission detector according to different variants.
Figure 6B:
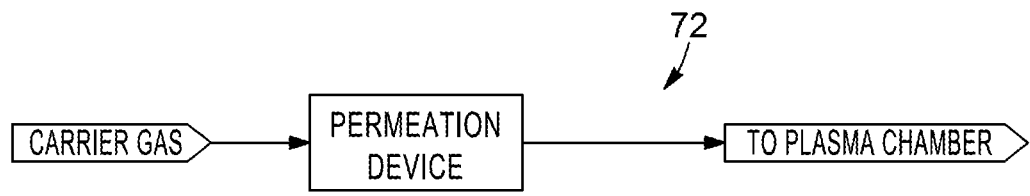
Figure 6C:
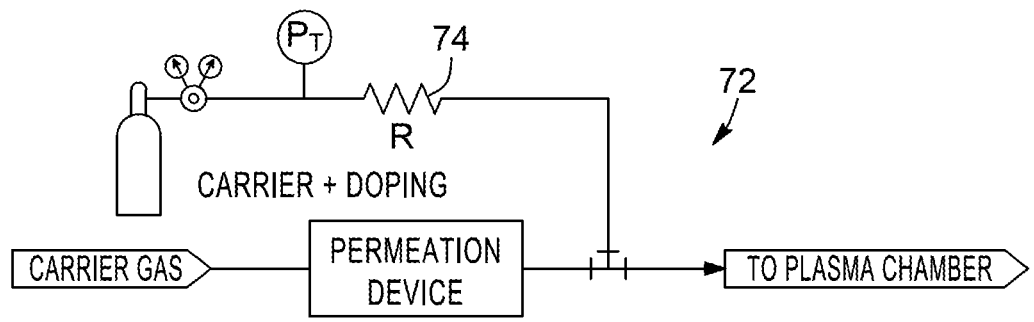

FIGS. 6A to 6D show four options of configurations for the plasma doping module 72 as known in the art. FIG. 6A illustrates one variant wherein the doping gas can be added to the sample to be analysed prior to its injection in the plasma chamber through an orifice 74 in the injection tubing 76 connected to the gas inlet of the plasma chamber. In the variant of FIG. 6B, the doping gas can be added to the gas to be analysed through a permeation device, for example allowing the dopants in the injection tubing 76 through a membrane. Both approaches mentioned above can be combined in a single plasma doping module 72, such as shown in FIG. 6C.

Figure 6D:
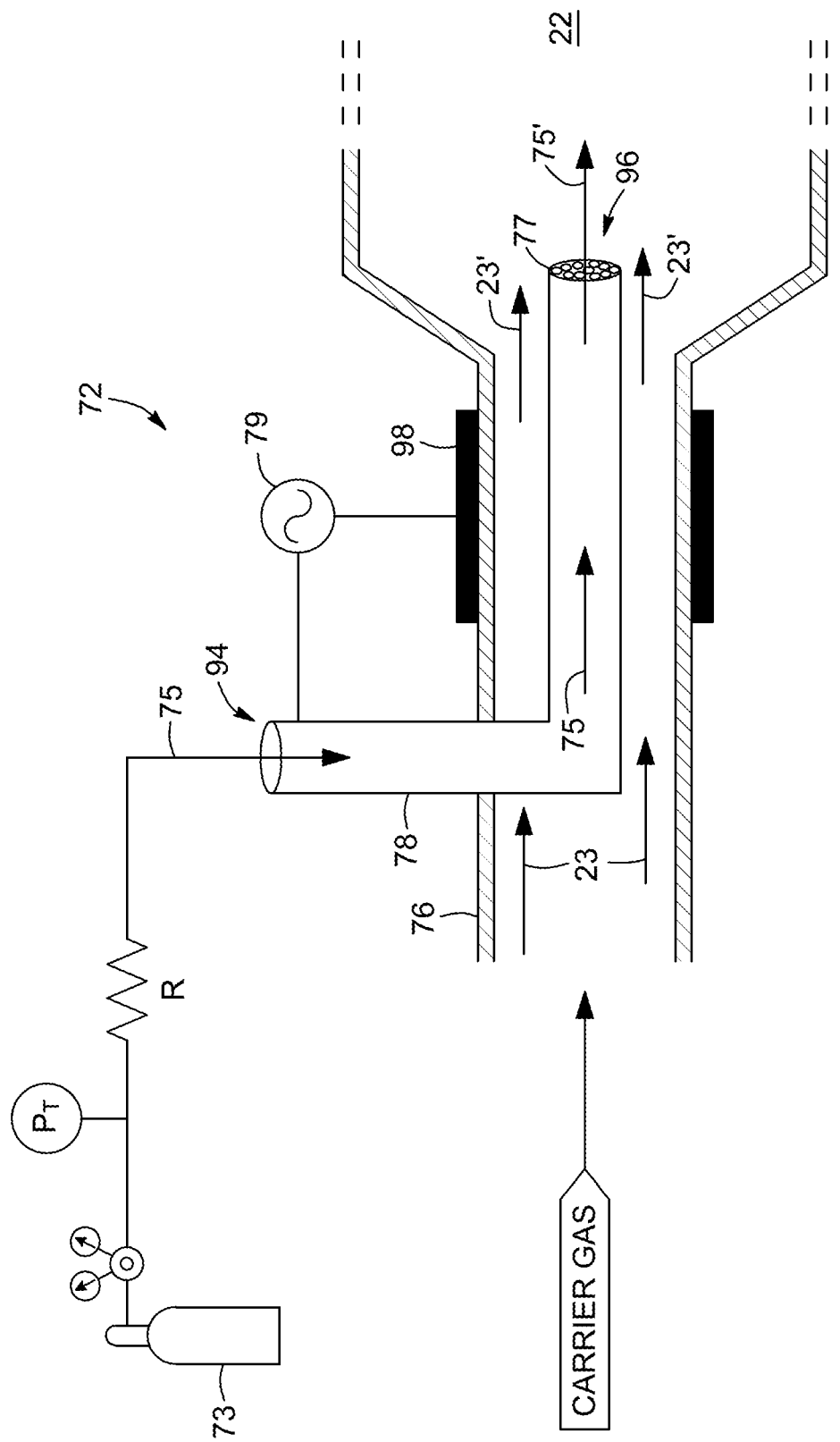

Finally, referring to FIG. 6D, there is shown on variant of a plasma doping module 72 allowing a pre-ionisation of the doping gas. In this variant, the plasma doping module 72 includes the injection tubing 76 connected to the plasma chamber 22 and carrying the flow of the gas sample 23 to the plasma chamber 22. An electrically conductive tube 78 extends within the injection tubing 76, for example concentrically. The electrically conductive tube 78 has an inlet 94 projecting out of the injection tubing 76 and connectable to a dopant source 73 to receive the flow of dopant gas 75, and an outlet 96 projecting within the plasma chamber 22 to output the flow of dopant gas 75 into the plasma chamber 22. A frit or metallic porous disc 77 may for example be welded to the outlet 96 of the electrically conductive tube 78 inserted inside the plasma chamber 22, allowing a more uniform distribution of the doping gas in the plasma chamber 22. Advantageously, the electrically conductive tube 78 can also act as an electrode, for example one of the electron-injecting electrodes described above. Preferably, a pre-ionisation electrode 98 is put in contact with the injection tubing 76 coextensively with the flow of dopant gas 75. For example, the pre-ionisation electrode 98 may be a tubular electrode surrounding a segment of the injection tubing 76. A pre-ionisation voltage source 79 is connected to the electrically conductive tube 78 and to the pre-ionisation electrode 98 to applying a voltage therebetween, through an AC or a DC pulsed driving signal. Advantageously, in such an embodiment the constituents of the doping gas can be "pre-ionised" as they enter the plasma chamber 22, therefore leading to an ionised or quasi-ionised dopant gas flow 75'. This approach can significantly reduce potential plasma-quenching effects. Furthermore, the gas sample flowing through the gas flow path 23 in the injection tubing 76 can also be pre-ionised by the electrical field across the injection tubing, facilitating the plasma-generating process in the chamber 22. Of course, the plasma doping module may have different configurations without departing from the scope of the invention.

Light Processing

Optical Emission Collection

With reference to FIG. 1, in the plasma chamber 22, the gas to be analysed undergoes a transformation under the applied plasma-generating field. Chemical compounds are ionised and decomposed by collisions with energetic electrons and molecules and atomic components are excited to higher energy levels, emitting radiation in the de-excitation process characteristic of the spectral properties of the species present in the gas sample. Processing this radiation can therefore provide information on the nature and relative concentration of the species in the gas to be analysed.

In the illustrated embodiment, radiation emitted from the gas to be analysed in the plasma chamber 22 can be transmitted out of the plasma chamber 22 through each one of the windows 24a to 24d. Preferably, the plasma-based detector 20 includes light collecting assemblies for collecting the light transmitted out of the plasma chamber 22 through each window 24a to 24d. In the illustrated configuration, each light collecting assembly includes an optical fiber 42a to 42d collecting light from a respective one of the windows 24a to 24d, and a lens 40a to 40d provided on the outside of the corresponding window 24a to 24d and focussing the radiation transmitted therethrough into the corresponding optical fiber 42a to 42d. It will be readily understood that other optical components collecting, guiding, transforming, or otherwise affecting light may additionally or alternatively be provided without departing from the scope of the present invention. Light transported by each optical fiber 24a to 24d is guided towards a light detection module 48 and a processing module 50 as will be explained further below.

Light Detection and Analysis

Figure 7:
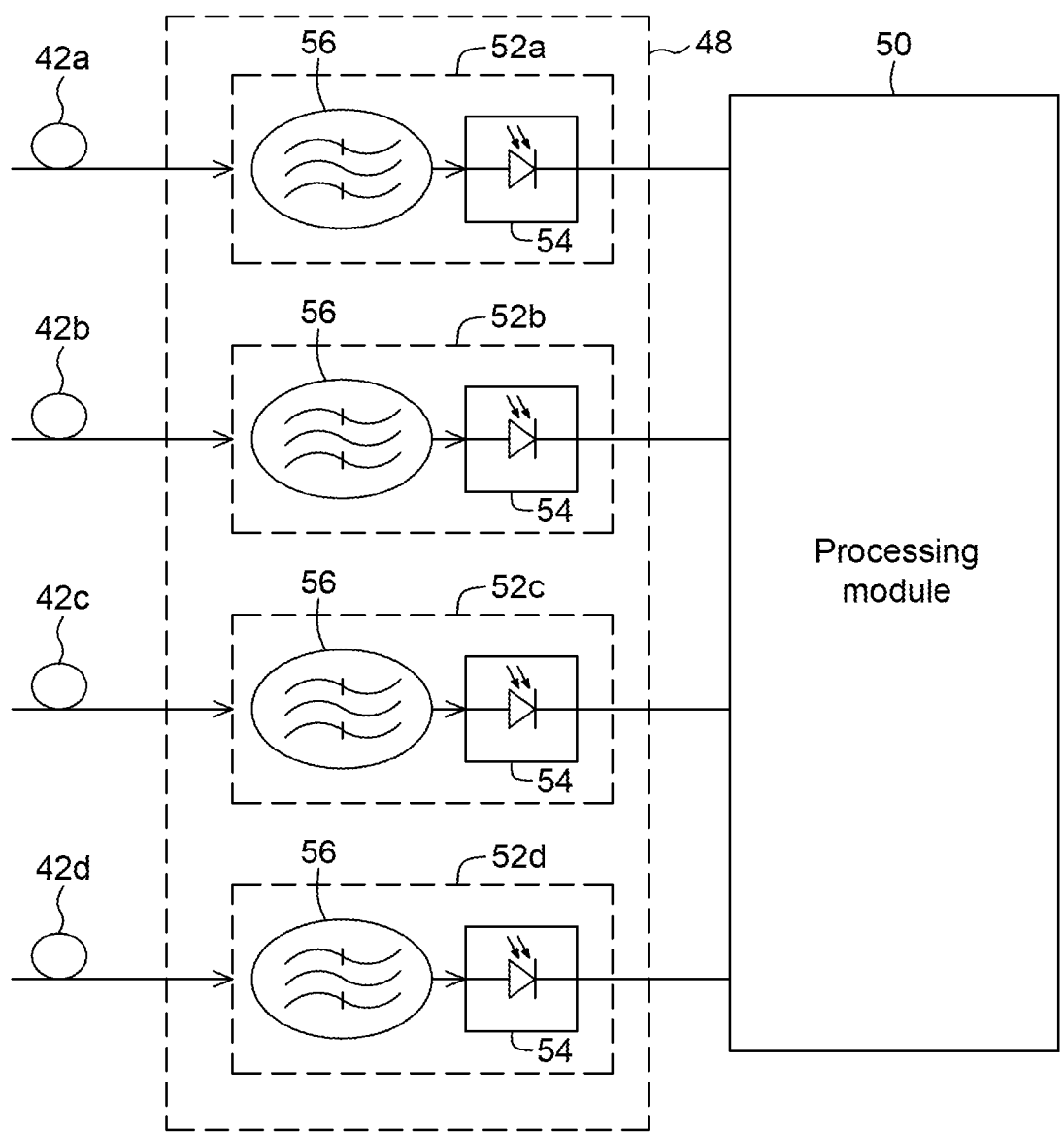
FIG. 7 is a schematized representation of a light detection module for use in a plasma-based optical emission detector according to one variant.

Referring to FIG. 7, the plasma-based detector further includes a light detection module 48 and a processing module 50 for respectively detecting and processing the radiation collected from the plasma chamber 22.

In one implementation, the light detection module 48 includes a plurality of detection cartridges 52a to 52d, each associated with the one of the windows of the plasma chamber and the corresponding light collecting assembly. Each detection cartridge 52a to 52d may for example include a photodiode 54 receiving light exiting one of the optical fibers 42a to 42d and converting the light to an electrical signal. The photodiode includes an operational amplifier having the required electronic gain. An optical filter 56 may be provided in between the output of the optical fiber 42 and the corresponding photodiode 54 to allow through only a spectral range of interest. Each optical filter may for example be embodied by an interferential filter or the like, and is preferably a bandpass filter centered on the wavelength or wavelength range to be monitored by the corresponding detection cartridge. It will be readily understood that in other variants different configurations could be used to extract the spectral information from the detected signals, such as for example using a spectrometer or other spectrally resolved detector to convert the optical energy into analog or digital information.

The processing module 50 may be embodied by any processor, computer, or the like apt to process the data obtained from the light detection module 48. It will be readily understood that the reference to a processing module in the singular is not meant to exclude systems including a plurality of components collaborating together to accomplished the desired processing function.

For example, in some embodiments the electric signal from each photodiode may be fed to an A/D converter and the digitally-converted signal data may be processed by a digital signal processor or a computer equipped with suitable data processing software. Data filtering and processing may therefore be performed digitally.

It will be readily understood that the processing of the information extracted from the collected light signals may involve any operation appropriate in view of the application and operation parameters of the plasma-based detector, and may include, non-limitatively, additions, subtractions, ratio calculations or any other mathematical functions. For example, baseline compensation could be obtained by subtracting from a given signal the light intensity associated with a wavelength next to the wavelength of interest, thereby eliminating the baseline upset caused by partially separate sample background. This can result in a cleaner baseline having well defined impurity peaks, making easier to integrate the area under those peaks, since they are baseline resolved.

Figure 8:
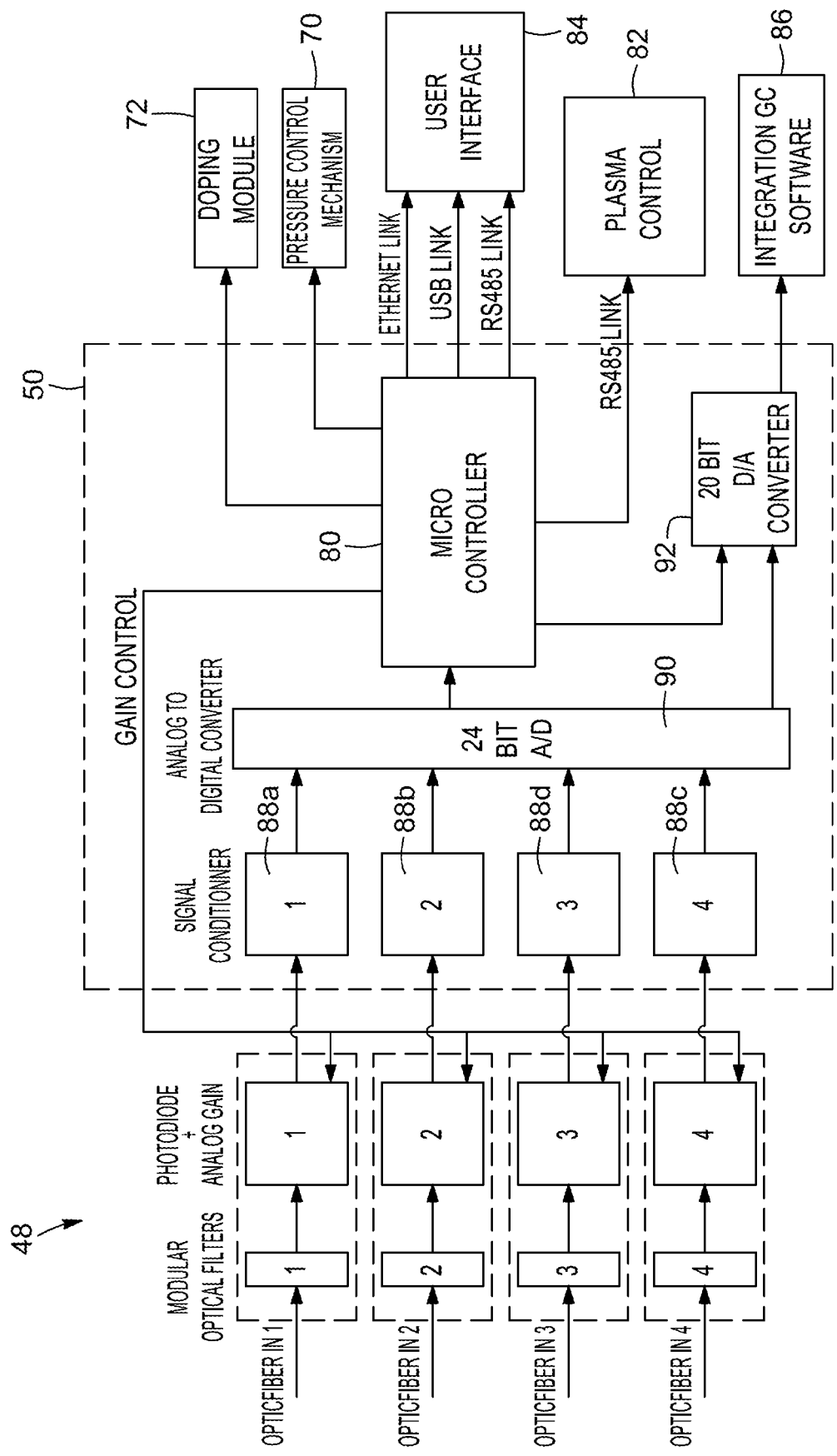
FIG. 8 is a block diagram of a processing module for use in a plasma-based optical emission detector according to one implementation.

Referring to FIG. 8, there is shown a functional diagram of the processing module 50 according to one implementation which supports multimode operation of a plasma-based optical emission gas detector according to some embodiments.

The processing module 50 first includes a microcontroller 80 generally providing processing capabilities to analyse the collected information from the optical emissions in the plasma and control the operation of the different component of the detector. For example, the microcontroller 80 may be in communication with the plasma controlling components 82 such as the plasma-generating mechanism, the plasma-localizing mechanism and the control of the electron-injection electrodes, with the pressure control mechanism 70 and the doping module 72. The microcontroller 80 may also be in communication with a user interface 84 and integration gas chromatography software 86.

In the illustrated embodiment, the processing module 50 includes a plurality of signal conditioning module 88a to 88d each associated with a corresponding optical channel of the light detection module 48. The microcontroller 80 may Each signal conditioning module 88a to 88d receives and the electrical signals from the light detection module 48 and processes these signals prior to transmission to the microcontroller 80. An analog-to-digital converter 90 converts the electrical signals in digital format prior transmission to the microcontroller 80.

In some implementations, the microcontroller 80 controls the operation parameters of the plasma-based detector based on a user defined timetable. Preferably, any of the system parameters can be changed in real time for each peak of a chromatogram signal, for example optical channel selection, system gain, plasma power, plasma pressure, electron injection intensity value etc. The microcontroller 80 allows for any arithmetic calculation between channels. For example, if an impurity peak elute on a decreasing or increasing baseline, due to an uncompleted sample background separation, it is possible to configure a second optical measuring channel to measure the emission spectrum baseline next to the wavelength of interest, then scale and subtract this signal from the impurity measuring channel. The result of this simple operation is used as the chromatogram and the signal is a baseline resolved or almost resolved peak.

The processing module 50 also provides a processed chromatogram analog output through a digital-to-analog converter 92 that can be used by a separate system for further processing.

The microcontroller 80 can also provide real-time signal trending and diagnostic functions. All operation parameters may be displayed in real-time, such as converter real-time value, voltage, temperature, pressure and flow. Real-time signal processing can be used for small peak signal recovery and Gaussian peak shape generation.

Multi-Mode Operation

In accordance with some implementations, the plasma-based detector described herein may be usable in accordance with one or more operation modes. Several such operation modes are described below. It will be understood that plasma-based detectors configured to operate in one, several or all of the operation modes described below may be considered within the scope of the present invention.

Emission Mode

In accordance with some implementations, the plasma-based optical emission detector may for example be operated in an emission mode, wherein the optical emissions correspond to gas species to be measured in the gas sample.

In this mode, one or more of the detection cartridge 52a to 52b may be designed and operated to detect light within a wavelength range associated with a species whose presence in the gas to be analysed is to be detected and measure. The design and data processing of the signal outputted by each cartridge may take under consideration the operation parameters of the components of the cartridge within the wavelength range of interest. For example, the electronic gain of a photodiode may be different based on the measurement wavelength. Typically, a UV enhanced photodiode has much lower gain or sensitivity in the UV range compared to its sensitivity in the visible range. As another example, the transmittance of an optical filter can be much lower in the UV range compared to a filter used in the visible range.

As one skilled in the art will readily understand, the light detection module and processing module may be adapted based on impurities to be measured and the carrier gases used in a given gas to be analysed.

In typical emission mode implementations, different emission zones may be monitored as a function of the composition of the gas to be analysed and the desired information.

For example, when using argon as carrier gas, the overall emission of argon is in the "red" spectral range. This could be monitored to report impurities flowing into the detector. Monitoring the overall intensities makes the detector more universal, meaning it gives a response to any impurity flowing into it. However, it may be desirable to make the detector more specific. In such case, some specific wavelengths or bands may be monitored. For example, the $O_2$ emission line at 777.7 nm, the $N_2$ emission line at 337.1 nm or the OH emission line at 305 nm (for moisture measurement) could be monitored to detect the presence of these specific impurities. Hydrocarbon measurements may for example be performed by monitoring the CH emission line at 454 nm. In some implementations, each light channel defined by a given set of window 24, optical fiber 42 and detection cartridge 52 may be particularly dedicated to the detection of a specific impurity. An example of the application of this feature is in air separation process, where the measurement of $N_2$ at low level has to be done in pure $O_2$. This is normally done by using a heartcut GC configuration, where the sample background, i.e. $O_2$, is vented away from the system. However, this process does not eliminate all the $O_2$ without generating excessive time delay. Making one of the detector channels specific to N2 (337.1 nm) substantially reduces response and baseline shifting due to O2 (777.7 nm) overload.

Indirect Impurity Detection

In other variants, the presence of impurities in the gas to be analysed may be measured indirectly. In such a mode, the gas species to be measured in the gas sample is detected through optical emissions associated with at least one dopant provided in the plasma chamber by the plasma doping module.

In accordance with one implementation, there is provided a method of measuring a gas species in a gas sample making use of a plasma doping strategy. Generally speaking, this method preferably involves the following step:
a) providing a plasma-based optical emission gas detector such as above, and/or at least including a plasma chamber and a plasma-generating mechanism configured to apply a plasma-generating field across the plasma chamber;
b) circulating the gas sample through the plasma chamber;
c) generating a plasma from the gas sample in the plasma chamber using the plasma-generating mechanism;
d) doping the gas sample in the plasma chamber with at least one dopant interacting with said gas species within the plasma; and
e) measuring optical emissions affected by the interacting of the at least one dopant with the gas species.

The method above may be used in the context of several applications. In some implementations, the optical emissions measured at step e) correspond to at least one spectral lines characteristic of the at least one dopant. For example, adding oxygen will generate a strong emission line at 777.7 nm. $O_2$ under plasma state is very reactive. The emission line could however decrease in a measurable fashion when an impurity is flowing into the plasma chamber. By way of example, if hydrocarbons are the gas species to be detected they will react with the oxygen in the plasma, reducing the amount of oxygen and, as a consequence, the strength of the $O_2$ emission line. Measuring a decrease in the line intensity can therefore provide information on impurities in the gas sample. Advantageously, the 777.7 nm $O_2$ emission line is within a spectral range where a band-pass filter having a good transmittance (>80%) and a photodiode giving a good response or signal (0.5 A/W compared to 0.08 A/W in the UV) can typically be easily found, allowing a reduction in the required electronic gain, advantageously reducing noise and drift. Doping with oxygen also has, in this particular case, another benefit; the oxygen can help keeping the plasma chamber clean by etching away carbon deposit on the wall and windows of the chamber.

In other implementations, the optical emissions may be spectral lines characteristic of the gas species that are affected by the interacting of this gas species with the at least one dopant. Indirect measurements could be of particular interest to detect impurities that do not give sufficient emission intensity, or have emission lines too close to emission lines from another element, making difficult to resolve them without using expensive echelle type spectrometers. Another example of the use of doping is to measure impurities emitting spectral lines of interest in the UV range, where detection may be difficult in some circumstances. This is for example the case for measuring $N_2$ as an impurity. Adding $O_2$ or $CO_2$ can provide a shift of the emitted radiation to the red portion of the spectrum, where standard photo-diode have a greater sensitivity.

In other implementations, the optical emissions measured at step e) correspond to at least one spectral line characteristic of a gas constituent by-product of the interacting of the at least one dopant with the gas species to be detected. In other words, the optical signature from a newly generated chemical compound or by-product resulting from the reaction of any particular impurities with a doping agent could be measure to indirectly report on impurity peak levels. Using oxygen as a dopant again by way of example only, reactions with hydrocarbon impurities will generate strong emission lines of CO and $CO_2$ in the infrared range and also in the low band. These strong emission lines could be used to increase overall system sensitivity.

Absorption Mode

In accordance with some implementations, the plasma-based detector may for example be operable in an absorption mode wherein absorption of an interrogation light beam through the plasma is measured.

By way of example, in this mode an interrogation light beam of a predetermined wavelength or spectral profile may be propagated through the plasma, for example, through one of the windows 24a, and light intensity at the interrogation wavelength is measured through the opposite window 24c. The detection cartridge associated with window 24c is preferably provided with a band-pass optical filter with a transmission range centered on the wavelength of the interrogation light beam.

One or more of the optical detection assembly associated with one of the windows of the plasma chamber may be replaced by an optical interrogation assembly (not shown) including components apt to inject an interrogation light beam of predetermined spectral characteristics through the plasma. For example, a diode-laser emission cartridge may be provided at one of the windows of the plasma chamber. In other variants one or more of the lenses and optical fibers shown in FIGS. 1 and 3 may be converted to an optical interrogation assembly by connecting a separate light source connected to the end of the optical fiber opposite the window.

As will be readily understood, in the absorption mode the level of absorption of interrogation light beam is measured. Proper selection of the spectral characteristics of the interrogation light beam can relate the measure signal variation to a specific impurity or a group of impurities in the gas to be analysed.

In some implementations, the wavelength of the interrogation light beam may be selected in the near infrared or infrared range. Many impurities are active in infrared; the plasma could be modulated ON and OFF to measure a differential signal. In some implementations, compensation for any drifting of the diode-laser emission cartridge can be performed. This may for example be accomplished at a time where there is no impurity flowing into the detector.

In some implementations, windows of the plasma chamber unused by the absorption mode detection process may be used in parallel in an emission mode such as described above. In this case, the diode-laser emission cartridge may be momentary turned off during the emission mode measurements, avoiding spectral interference.

Constant Emission Mode

In accordance with some implementations, the plasma-based detector may be operable in a constant emission mode, wherein the light detection is used to continuously monitor the optical emissions from the plasma and a frequency of the plasma-generating mechanism is adjusted to maintain these optical emissions constant, the gas species to be measured in the gas sample being detected through a variation in said frequency.

When impurity levels are high, for example in the percentage range, plasma power distribution and impedance are changed, and it can be more difficult to maintain the position of the plasma. In accordance with one aspect, the plasma-based detector may be used in the constant emission mode (also referred to as "power balance mode") to improve performance in such conditions.

In according with one implementation, there is therefore provided a method of measuring impurities in a gas sample which involves using a plasma-based optical emission gas detector such as described herein in a constant emission or power balance mode. The plasma-based optical emission detector is assumed to include a plasma chamber and a plasma-generating mechanism having a pair of discharge electrodes and an alternating current generator providing an alternating discharge driving signal to the discharge electrodes at an adjustable frequency. The method involves circulating the gas sample through the plasma chamber and generating a plasma from the carrier gas in the plasma chamber using the plasma-generating mechanism, as explained above. The method also involves continuously measuring an optical emission from the plasma, for example using a dedicated optical channel of the plasma-based detector, to monitor the overall intensity of the plasma. In some implementations, the optical emissions being measured may consist in a spectral line of the impurities to be measured, using an optical channel designed for a specific wavelength or a spectral range associated with the spectral line. In other implementations the optical emissions being measured may consist in a broad spectrum light emitted by the plasma and representative of several constituents of the gas sample, including the impurities to be measured.

Using the monitored optical emissions as a reference signal, the plasma power can be fixed to an appropriate value, through a proper control of the operating conditions. To achieve this control, the method involves adjusting the frequency of the discharge driving signal in real time to maintain the measured optical emission constant. For example, the frequency can be converted to a voltage value representing the applied voltage between the discharge electrodes. This voltage may be zeroed prior to the introducing of the time-separated peaks. Upon arrival of an impurity peak in the plasma chamber, the intensity of the monitored emission line changes. The plasma power can be adjusted manually or automatically upon this change in order to maintain constant the monitored emission. Monitoring the frequency of the discharge driving signal provides a detection of the gas species through variations in this frequency.

Figure 9:
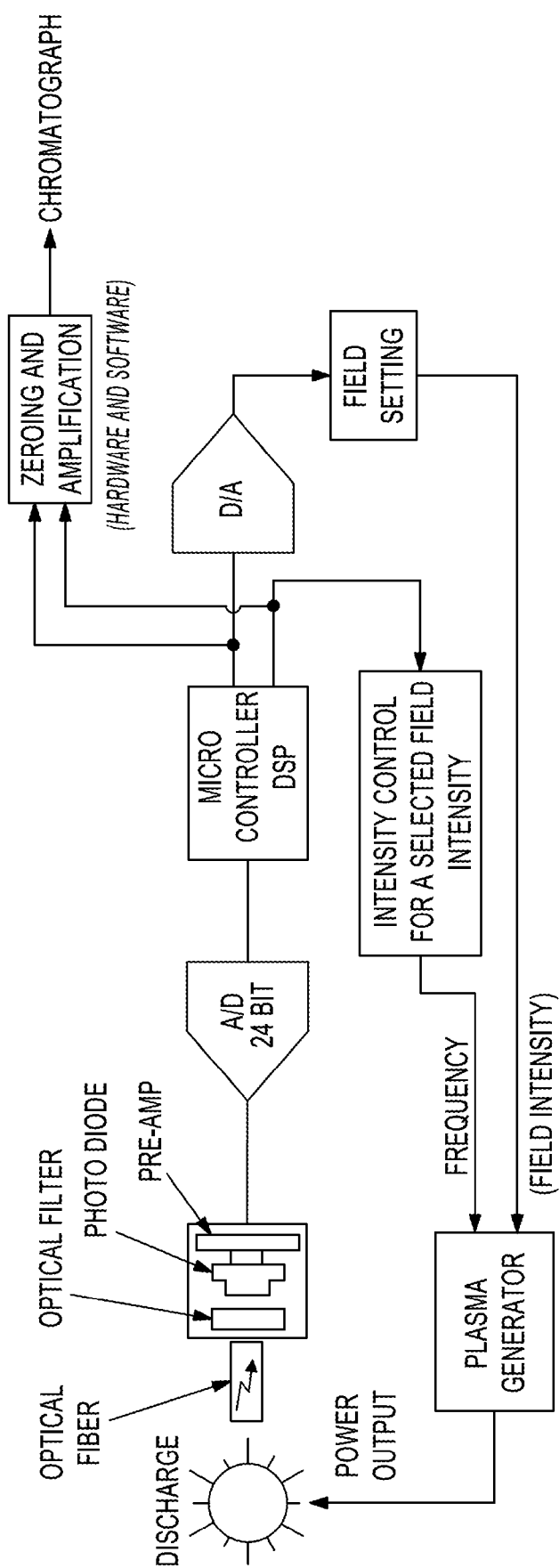
FIG. 9 is a block diagram of a configuration which may be used to enable a constant emission mode according to one implementation.

Referring to FIG. 9, there is shown schematically a configuration which may be used to enable a constant emission mode according to one implementation. A correction signal is nulled before the impurities arrive in the plasma zone. The correction signal is amplified and fed to an A/D converter and the data is processed to generate the % value of impurities. In this mode, the detector is capable of replacing the thermal conductivity detector (TCD) used in such application, i.e. high level of impurity measurement.

Depending on which wavelength band or spectral zone used to control and maintain the plasma intensity, the correction could be negative or positive, since the emission could increase or decrease with impurity level. Also, for the same reason, the correction signal could be linearly related to plasma emission or not. The data processing system is used to treat various possible situations. When used in power balance mode, to report impurity quantity, other optical channels could be used to qualify the impurities, i.e. to identify it based on wavelength generated.

As one skilled in the art will readily understand, detectors according to implementations such as described above may advantageously provide for the detection of impurities in different carrier gases using a same device. Advantageously, the detector may enable a switch between different chromatographic stream operating with different carrier gases in real time.

Detectors used in gas chromatography systems are generally configured in view of use with one carrier gas species. When a change of carrier gas is desired the background of the sample must be separated or vented away from the detector, to avoid overloading the detector which would require some time for recovery. Standard heartcut, or backflush, GC configurations can be used for this purpose. These configurations require multiple columns and valves, which contributes to impurities peak broadening. By contrast, the detector according to embodiments described herein may be switch from operation with one carrier gas to another through a simple static purge of the gas in the detector and change of the operation parameters in view of the incoming carrier gas.

Of course, numerous modifications could be made to the embodiments described above without departing from the scope of the present invention.

The invention claimed is:

1. A plasma-based optical emission gas detector, comprising:
    a plasma chamber traversed by a gas flow path allowing a flow of a gas sample through the plasma chamber;
    a plasma-generating mechanism configured to apply a plasma-generating field across the plasma chamber intersecting the gas flow path so as to generate a plasma from said gas sample;
    at least one optical window allowing optical emissions from said plasma to exit the plasma chamber therethrough; and
    a plasma-localizing mechanism configured to apply a plasma-localizing field across the plasma chamber and positioned such that the plasma-localizing field localizes the plasma within the plasma chamber in alignment with the at least one optical window.

2. The plasma-based optical emission gas detector according to claim 1, wherein the plasma-localizing field is applied transversally to the plasma-generating field.

3. The plasma-based optical emission gas detector according to claim 1, wherein the plasma-generating mechanism relies on a Dielectric Barrier Discharge.

4. The plasma-based optical emission gas detector according to claim 3, wherein the plasma-generating mechanism comprises:
    a pair of discharge electrodes extending parallelly on opposite sides of the plasma chamber and separated by a discharge gap;
    a pair of insulating dielectric barriers each extending within the discharge gap along a corresponding one of the discharge electrodes; and
    an alternating current generator providing an alternating discharge driving signal to the discharge electrodes.

5. The plasma-based optical emission gas detector according to claim 4, wherein each insulating layer of said pair is defined by a wall of the plasma chamber.

6. The plasma-based optical emission gas detector according to claim 5, wherein the plasma chamber comprises a pair of opposite first walls associated with the plasma-generating mechanism and a pair of opposite second walls transversal to the first walls and associated with the plasma-localizing mechanism.

7. The plasma-based optical emission gas detector according to claim 5, wherein the plasma chamber has an hexagonal configuration defining top and bottom walls associated with the plasma-generating mechanism, a pair of opposite sides walls associated with the plasma-localizing mechanism and four remaining side walls each associated with one of the at least one window.

8. The plasma-based optical emission gas detector according to claim 4, wherein the plasma-localizing mechanism comprises a pair of localizing electrodes extending parallelly on opposite sides of the plasma chamber, the plasma-localizing field being an electrical field.

9. The plasma-based optical emission gas detector according to claim 8, wherein the plasma-localizing mechanism further comprises a power supply configured to apply a DC localizing drive signal on the localizing electrodes.

10. The plasma-based optical emission gas detector according to claim 8, wherein the plasma-localizing mechanism comprises a power supply configured to apply a localizing drive signal on the localizing electrodes, the localizing drive signal comprising a DC component and an AC component synchronized with the discharge driving signal.

11. The plasma-based optical emission gas detector according to claim 10, wherein the localizing driving signal is controllable to align the plasma with a selected one of the at least one window in synchronicity with a passage of a predetermined impurity peak in the gas sample along the gas flow path.

12. The plasma-based optical emission gas detector according to claim 1, wherein the plasma-localizing mechanism comprises a pair of electromagnets extending parallelly on opposite sides of the plasma chamber, the plasma-localizing field being a magnetic field.

13. The plasma-based optical emission gas detector according to claim 1, further comprising a pair of electron-injecting electrodes, each electrode of said pair having an extremity projecting within the plasma.

14. The plasma-based optical emission gas detector according to claim 13, wherein each electron-injecting electrode has a needle or a flat-tip shape.

15. The plasma-based optical emission gas detector according to claim 13, wherein the extremities of the electron-injecting electrodes of said pair project within the plasma chamber from opposite sides thereof.

16. The plasma-based optical emission gas detector according to claim 13, comprising a gas inlet and a gas outlet defining opposite ends of said gas flow path, each of the electron-injection electrodes of said pair being inserted in the plasma chamber through a respective one of the gas inlet and gas outlet.

17. The plasma-based optical emission gas detector according to claim 1, further comprising a pressure control mechanism configured to control a pressure within the plasma chamber over a continuous pressure range.

18. The plasma-based optical emission gas detector according to claim 17, wherein the continuous pressure range substantially extends between vacuum pressure and atmospheric pressure.

19. The plasma-based optical emission gas detector according to claim 1, further comprising:
at least one light-collecting assembly, each light collecting assembly collecting the optical emissions from said plasma exiting the plasma chamber through a corresponding one of the at least one window;
a light detection module configured to detect the optical emissions collected by the at least one light-collecting assembly; and
a processing module configured to process the optical emissions detected by the light detection module.

20. The plasma-based optical emission gas detector according to claim 19, wherein each of the at least one light collecting assembly comprises:
an optical fiber collecting light from the corresponding one of the at least one window; and
a lens provided on outside of the corresponding one of the at least one window and focussing the optical emissions transmitted therethrough into the corresponding optical fiber.

21. The plasma-based optical emission gas detector according to claim 19, wherein the light detection module comprises at least one detection cartridge, each detection cartridge detecting the optical emissions collected by a corresponding one of the at least one light-collecting assembly.

22. The plasma-based optical emission gas detector according to claim 21, wherein each detection cartridge comprises a photodiode converting the corresponding optical emissions into an electrical signal.

23. The plasma-based optical emission gas detector according to claim 20, wherein each of the at least one light collecting assembly or each of the at least one detection cartridge includes an optical filter transmitting through only a spectral range of interest.

24. The plasma-based optical emission gas detector according to claim 1, wherein the at least one window consists in a plurality of windows, each of said windows being associated with optical emissions in a different spectral range.

25. The plasma-based optical emission gas detector according to claim 24, wherein the plasma-localizing mechanism is further configured to adapt the plasma-localizing field to align the plasma with a selected one of said windows in synchronization with a passage of a gas species emitting in the corresponding spectral range through the plasma chamber.

26. The plasma-based optical emission detector according to claim 1, further comprising a plasma doping module configured to inject at least one dopant species to the gas sample flowing through the plasma chamber.

27. The plasma-based optical emission detector according to claim 26, further comprising an injection tubing carrying the gas sample to the plasma chamber, and wherein the plasma doping module comprises an orifice in said injection tubing.

28. The plasma-based optical emission detector according to claim 26, wherein the plasma doping module comprises a permeation device.

29. The plasma-based optical emission detector according to claim 26, wherein the plasma doping module comprises an electrically conducting tube inserted into the plasma chamber.

30. The plasma-based optical emission detector according to claim 1, further comprising:
a pressure control mechanism configured to control a pressure within the plasma chamber over a continuous pressure range;
a plasma doping module configured to inject at least one dopant species to the gas sample flowing through the plasma chamber at least one light-collecting assembly, each light collecting assembly collecting the optical emissions from said plasma exiting the plasma chamber through a corresponding one of the at least one window;
a light detection module configured to detect the optical emissions collected by the at least one light-collecting assembly; and a processing module configured to process the optical emissions detected by the light detection module, the processing module comprising a microcontroller in communication with the plasma-generating mechanism, the plasma-localizing mechanism, the pressure control mechanism and the plasma doping module.

31. The plasma-based optical emission detector according to claim 30, operable at least one of a plurality of modes comprising:
an emission mode wherein said optical emissions correspond to gas species to be measured in the gas sample;
an absorption mode wherein absorption of an interrogation light beam through the plasma is measured;
an indirect detection mode wherein the gas species to be measured in the gas sample is detected through optical emissions associated with at least one dopant provided in the plasma chamber by the plasma doping module; and
a constant emission mode wherein the light detection is used to continuously monitor the optical emissions from the plasma and a frequency of the plasma-generating mechanism is adjusted to maintain said optical emissions constant, the gas species to be measured in the gas sample being detected through a variation in said frequency.

32. The plasma-based optical emission detector according to claim 31, operable in all of the modes of said plurality of modes.

33. A plasma-based gas detector, comprising:
a plasma chamber traversed by a gas flow path allowing a flow of a gas sample through said plasma chamber;
a plasma-generating mechanism configured to apply a plasma-generating field across the plasma chamber, the plasma-generating field intersecting the gas flow path so as to generate a plasma from said gas sample, the plasma occupying a plasma region within the plasma chamber; and
a pair of electron-injecting electrodes, each electrode of said pair having an extremity projecting within the plasma region.

34. The plasma-based gas detector according to claim 33, wherein each electron-injecting electrode has a needle or a flat-tip shape.

35. The plasma-based gas detector according to claim 33, wherein the extremities of the electron-injecting electrodes of said pair project within the plasma chamber from opposite sides thereof.

36. The plasma-based gas detector according to claim 33, comprising a gas inlet and a gas outlet defining opposite ends of said gas flow path, each of the electron-injection electrodes of said pair being inserted in the plasma chamber through a respective one of the gas inlet and gas outlet.

37. The plasma-based gas detector according to claim 33, further comprising a pressure control mechanism configured to control a pressure within the plasma chamber.

38. The plasma-based gas detector according to claim 33, wherein at least one of said electron-injecting electrodes comprises an electrically conducting tube inserted into the plasma chamber and connectable to a dopant source to inject at least one dopant species to the gas sample flowing through the plasma chamber.

39. A method for generating a plasma in a plasma chamber of a plasma-based gas detector, the method comprising:
a) circulating a flow of a gas sample through the plasma chamber;
b) controlling a pressure inside the plasma chamber to a sub-atmospheric level;
c) applying a plasma-generating field across the plasma chamber intersecting the flow of gas sample so as to generate a plasma from the gas sample;
d) putting respective extremities of a pair of electron-injecting electrodes in contact with the plasma; and
e) applying a voltage on the electron-injecting electrode such that free electrons are injected within the plasma chamber.

40. A method of detecting a gas species in a gas sample, comprising:
a) providing a plasma-based optical emission gas detector comprising a plasma chamber and a pressure control mechanism operable to control a pressure in the plasma chamber over a continuous pressure range;
b) selecting a pressure setting based on at least one sample characteristic associated with the gas sample;
c) circulating a flow of the gas sample through the plasma chamber;
d) generating a plasma from the gas sample in the plasma chamber;
e) controlling the pressure control mechanism to maintain the pressure in the plasma chamber at the selected pressure setting; and
f) measuring optical emissions from the plasma indicative of presence of the gas species.

41. The method according to claim 40, wherein the continuous pressure range substantially extends between vacuum pressure and atmospheric pressure.

42. The method according to claim 40, wherein the at least one sample characteristic comprises a volume of the gas sample flowing through the plasma chamber.

43. The method according to claim 40, wherein the at least one sample characteristic comprises an excitation potential of the gas species.

44. The method according to claim 40, wherein the at least one sample characteristic comprises a target residence time of the gas species in the plasma chamber.

45. The method according to claim 40, wherein the pressure setting is selected in view of tuning an internal volume of the plasma chamber.

46. The method according to claim 40, wherein the gas species has an ionization potential higher than an ionization potential of a carrier gas carrying said gas species though the plasma chamber.

47. The method according to claim 40, wherein the controlling of step e) comprises using a feedback control loop.

48. The method according to claim 47, wherein the feedback control loop comprises measuring a pressure of the gas sample downstream the plasma chamber and operating a pump in the pressure control mechanism if view of the measured pressure.

49. The method according to claim 40, wherein the measuring of step f) comprises measuring an intensity of said optical emissions at one or more wavelengths characteristic of the gas species.

50. The method according to claim 40, wherein the generating a plasma of step of d) comprises:
i. putting respective extremities of a pair of electron-injecting electrodes in contact with the plasma; and
ii. applying a voltage on the electron-injecting electrode such that free electrons are injected within the plasma chamber.

51. A method of measuring a gas species in a gas sample, comprising:
a) providing a plasma-based optical emission gas detector comprising a plasma chamber and a plasma-generating mechanism comprising a pair of discharge electrodes and an alternating current generator providing an alternating discharge driving signal to the discharge electrodes at an adjustable frequency;

b) circulating the gas sample through the plasma chamber;

c) generating a plasma from the carrier gas in the plasma chamber using the plasma-generating mechanism;

d) continuously measuring an optical emission from the plasma and adjusting the frequency of the discharge driving signal in real time to maintain the measured optical emission constant;

e) introducing time-separated peaks of said impurities in the flow of carrier gas; and f) monitoring the frequency of the discharge driving signal and detecting the gas species through variations in said frequency.

52. The method according to claim 51, wherein the monitoring of step f) comprises converting said frequency to a voltage value.

53. The method according to claim 52, comprising zeroing the voltage value prior to the introducing of the time-separated peaks.

54. The method according to claim 51, wherein the optical emissions measured at step d) consist in a spectral line of the gas species to be measured.

55. The method according to any claim 51, wherein the optical emissions measured at step d) consist in broad spectrum light emitted by the plasma.

56. A method of measuring a gas species in a gas sample, comprising:
providing a plasma-based optical emission gas detector comprising a plasma chamber and a plasma-generating mechanism configured to apply a plasma-generating field across the plasma chamber;
circulating the gas sample through the plasma chamber;
generating a plasma from the gas sample in the plasma chamber using the plasma-generating mechanism;
doping the gas sample in the plasma chamber with at least one dopant interacting with said gas species within the plasma; and
measuring optical emissions affected by said interacting of the at least one dopant with the gas species.

57. The method according to claim 56, wherein the optical emissions measured at step e) correspond to at least one spectral line characteristic of the at least one dopant.

58. The method according to claim 56, wherein the optical emissions correspond to at least one spectral line characteristic of the gas species that are affected by the interacting of said gas species with the at least one dopant.

59. The method according to claim 56, wherein the optical emissions measured at step e) correspond to at least one spectral line characteristic of a gas constituent by-product of the interacting of the at least one dopant with the gas species to be detected.

60. A plasma doping module for a plasma-based optical emission gas detector comprising a plasma chamber traversed by a gas flow path allowing a flow of a gas sample through the plasma chamber, the plasma doping module comprising:
an injection tubing connected to the plasma chamber and carrying said flow of the gas sample to the plasma chamber;
an electrically conductive tube extending within the injection tubing, the electrically conductive tube having an inlet projecting out of the injection tubing and connectable to a dopant source to receive a flow of dopant gas therefrom, and an outlet projecting within the plasma chamber to output said flow of dopant gas into said plasma chamber;
a pre-ionisation electrode in contact with the injection tubing coextensively with the flow of dopant gas; and
a pre-ionisation voltage source connected to the electrically conductive tube and to the pre-ionisation electrode to apply a voltage therebetween, thereby pre-ionising the flow of dopant gas.

61. The plasma doping module according to claim 60, wherein the pre-ionisation electrode is a tubular electrode surrounding a segment of the injection tubing.

62. The plasma doping module according to claim 60, further comprising a frit or a metallic porous disc at the outlet of the electrically conductive tube.

63. The plasma doping module according to claim 60, wherein the pre-ionisation voltage source generates an AC or a pulsed pre-ionisation driving signal.

* * * * *